US010899885B2

(12) United States Patent
Joy et al.

(10) Patent No.: US 10,899,885 B2
(45) Date of Patent: Jan. 26, 2021

(54) VEGETABLE OIL BASED VISCOELASTIC POLYMERS THAT DISPLAY PHOTORESPONSIVE RHEOLOGICAL AND ADHESIVE PROPERTIES

(71) Applicants: Abraham Joy, Copley, OH (US); Ying Xu, Nanjing (CN); Sudhanva Raj Govindarajan, Elgin, IL (US); John Swanson, Cleveland, OH (US)

(72) Inventors: Abraham Joy, Copley, OH (US); Ying Xu, Nanjing (CN); Sudhanva Raj Govindarajan, Elgin, IL (US); John Swanson, Cleveland, OH (US)

(73) Assignee: The University of Akron, Akron, OH (US)

( * ) Notice: Subject to any disclaimer, the term of this patent is extended or adjusted under 35 U.S.C. 154(b) by 323 days.

(21) Appl. No.: 15/513,252

(22) PCT Filed: Sep. 22, 2015

(86) PCT No.: PCT/US2015/051453
§ 371 (c)(1),
(2) Date: Mar. 22, 2017

(87) PCT Pub. No.: WO2016/049029
PCT Pub. Date: Mar. 31, 2016

(65) Prior Publication Data
US 2017/0298183 A1    Oct. 19, 2017

Related U.S. Application Data

(60) Provisional application No. 62/053,302, filed on Sep. 22, 2014.

(51) Int. Cl.
  *C08G 71/04* (2006.01)
  *C08G 18/32* (2006.01)
  *C09J 175/12* (2006.01)
  *C07D 311/16* (2006.01)

(52) U.S. Cl.
  CPC ............ *C08G 71/04* (2013.01); *C07D 311/16* (2013.01); *C08G 18/3293* (2013.01); *C09J 175/12* (2013.01)

(58) Field of Classification Search
  CPC .... C08G 63/00; C08G 18/3293; C08G 71/04; C08G 18/3275; C08G 18/3825; C08G 18/73; C08G 63/685; C08G 63/6856; C08G 63/91; C08G 63/916; C08G 73/0233; C07D 311/16; C09J 175/12
  See application file for complete search history.

(56) References Cited

U.S. PATENT DOCUMENTS

| 3,447,916 | A | 6/1969 | Edwards |
| 9,663,614 | B2* | 5/2017 | Joy ................. C07D 311/18 |
| 2015/0094422 | A1* | 4/2015 | Joy ................. C08G 63/6856 525/54.1 |
| 2017/0298183 | A1* | 10/2017 | Joy ................. C08G 18/3293 |

FOREIGN PATENT DOCUMENTS

| WO | 2013130985 A1 | 9/2013 |
| WO | 2014074845 A1 | 5/2014 |
| WO | 2015067833 | 5/2015 |

OTHER PUBLICATIONS

Z.Nofal et al Synthesis and chemoprophylactic effect of novel coumarin derevatives, Egyptian Journal of Chemistry (2005), 48(5), 587-604—Abstract.*
Atkins et al "A Versatile Approach for the Syntheses of Poly(esteramide)s with Pendant Functional Groups" Journal of Polymer Science: Part A: Polymer Chemistry, vol. 47, 3757-3772 (2009) (Year: 2009).*
Pasparakis et al "Photodegradable Polymers for Biotechnological Applications"Macromol. Rapid Commun. 2012, 33, 183-198 (Year: 2012).*
Chujo et al "Polyoxazoline Having a Coumarin Moiety as a Pendant Group" (Year: 1990).*
Database CA Chemical Abstracts Service—Mohan, R.R. et al: "Synthesis and anthelmintic activity of 4-methyl-7-(substituted phenylaminocarbonyl/disubstituted aminocarbonyl)methoxycoumarins", STN Database accession No. 1984:610928; & Mohan, R.R. et al: "Synthesis and anthelmintic activity of 4-methyl-7-(substituted phenylaminocarbonyl/disubstituted aminocarbonyl)methoxycoumarins", Indian Drugs, 21(9), 389-92 CODEN: INDRBA; ISSN: 0019-462X, 1984.
EPO Office Action in application 15843956.2; dated May 13, 2020.

* cited by examiner

*Primary Examiner* — Ling Siu Choi
*Assistant Examiner* — Gennadiy Mesh
(74) *Attorney, Agent, or Firm* — Renner Kenner Greive Bobak Taylor and Weber

(57) ABSTRACT

Photoresponsive polymers that comprise a unit derived from an amide functional diol compound that includes a coumarin group are provided. Advantageously, the photoresponsive groups of the photoresponsive polymers may be used to control the viscosity of the photoresponsive polymer. The photoresponsize polymers may also include units derived from amide functional diol compounds with include a fatty acid chain or a polyethylene glycol chain. The photoresponsive polymers may be used for 3d printing. When an adhesive group is added to a photoresponsive polymer they may be used as an adhesive. Adhesive groups include catechol groups.

11 Claims, 8 Drawing Sheets

VEGETABLE OIL BASED VISCOELASTIC POLYMERS THAT DISPLAY PHOTORESPONSIVE RHEOLOGICAL AND ADHESIVE PROPERTIES

CROSS-REFERENCE TO RELATED APPLICATIONS

The present application claims priority to PCT App. No. US2015/051453 filed on Sep. 22, 2015, which claims priority to U.S. Provisional Patent Application No. 62/053,302, filed Sep. 22, 2014, all of which are incorporated herein by reference.

FIELD OF THE INVENTION

One or more embodiments provide photoresponsive polymers that comprise a unit derived from an amide functional diol compound that includes a coumarin group. Embodiments also include methods of 3D printing photoresponsive polymers.

BACKGROUND OF THE INVENTION

Coumarin derivatives have found extensive applications as optical bleaching agents, fluorescence labels, and photo responsive units on polymeric systems. The photochemistry of coumarin derivatives has been extensively studied. Coumarin derivatives such as 7-methoxycoumarin can undergo [2+2] photocycloaddition to yield cyclobutane dimers upon irradiation around 350 nm. The cycloaddition reaction is reversible when irradiated at a shorter wavelength. Coumarin derivatives can also react with olefins through [2+2] photocycloaddition.

Vegetable oils are renewable resources that have been used as raw material in many manufactured products such as soaps, candles, perfumes and lubricants. The use of vegetable oils in polymer materials has gained increasing interest because of their sustainability and low cost. Many applications have been explored for use in industry, including the synthesis of neem-oil-based polyurethane coatings. Others have explored coatings made from soybean oils. Pressure sensitive adhesives from epoxidized and dihydroxyl soybean oils have also been synthesized and studied.

Catechol is a molecule derived by the secretion-based adhesion of marine mussels to wet rocks in harsh marine environments. Mussel foot proteins have been extensively studied to understand wet adhesion mechanisms. Such studies have inspired the research and development of synthetic wet adhesives. Among these are 3,4-dihydroxyphenyl-L-alanine (DOPA), a posttranslational amino acid of tyrosine, found naturally in mussel food proteins in varying concentrations. This molecule is believed to play an important role in wet adhesion and cohesion of byssus (adhesive filaments) through cation-n, n-n stacking and hydrophobic interactions. Catechol, also known as 1,2-dihydroxybenzene, is the isolated functional end of DOPA. While DOPA and catechol have been explored in many polymeric synthesis routes for adhesive applications, these synthetic routes yield nondegradable polymers, limiting their applications in the biomedical field.

SUMMARY OF THE INVENTION

In a first embodiment a polymer is provided comprising a unit derived from an amide functional diol compound that includes a coumarin group; and a unit derived from an amide functional diol compound that includes a fatty acid chain.

In a second embodiment a polymer is provided as in the first embodiment, where the nitrogen atoms the functional diol compounds are part of the backbone of the polymer.

In a third embodiment a polymer is provided as in either the first or second embodiment, where the polymer further comprises a unit derived from an amide functional diol compound that includes a catechol group or a protected catechol group.

In a fourth embodiment a polymer is provided as in any of the first through third embodiments, where the polymer is a polyester or a polyurethane.

In a fifth embodiment a polymer is provided as in any of the first through forth embodiments, where the polymer includes a unit derived from a dicarboxylic acid.

In a sixth embodiment a polymer is provided as in any of the first through fifth embodiments, where the polymer includes a unit derived from a diisocyanate.

In a seventh embodiment a polymer is provided as in any of the first through sixth embodiments, where the unit derived from an amide functional diol compound that includes a coumarin group is defined by the formula:

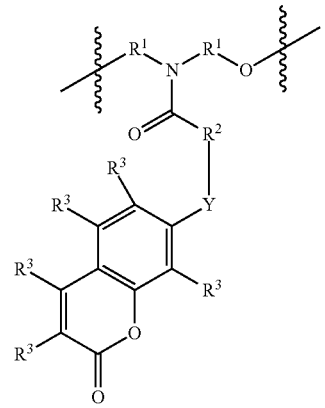

where each $R^1$ is individually a hydrocarbon group, $R^2$ is a hydrocarbon group; each $R^3$ is individually a hydrogen atom, a halogen atom or an alkoxy group, and Y is an oxygen atom or an amide group.

In an eighth embodiment a polymer is provided as in any of the first through seventh embodiments, where the unit derived from an amide functional diol compound that includes a fatty acid chain is defined by the formula:

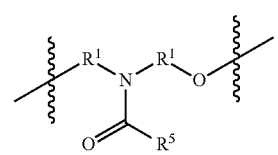

where each $R^1$ is individually a hydrocarbon group and $R^5$ is the carbon chain of fatty acid.

In a ninth embodiment a polymer is provided as in any of the first through eighth embodiments, where unit derived from an amide functional diol compound that includes catechol group or a protected catechol group is defined by the formula:

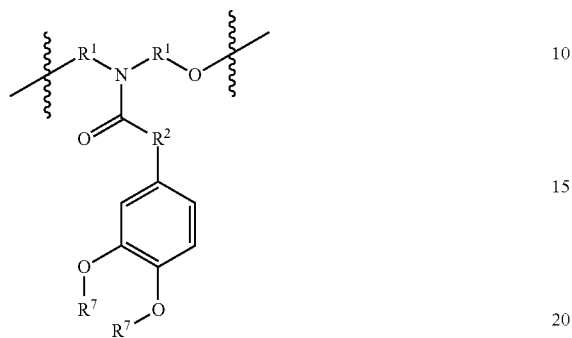

where each $R^1$ is individually a hydrocarbon group; $R^2$ is a hydrocarbon group; and each $R^7$ is individually a hydrogen atom or an organic group, or where the two $R^7$ groups combine to make a single organic group.

In a tenth embodiment a polymer is provided as in any of the first through ninth embodiments, where the polymer is defined by the formula

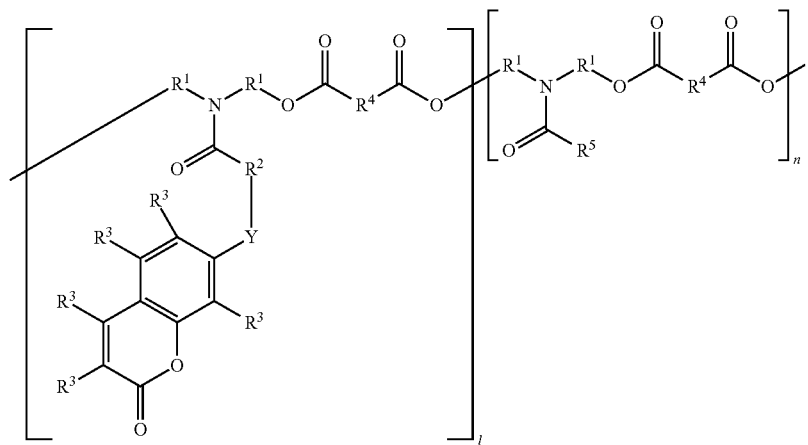

where each $R^1$ is individually a hydrocarbon group, $R^2$ is a hydrocarbon group; each $R^3$ is individually a hydrogen atom, a halogen atom or an alkoxy group; Y is an oxygen atom or an amide group; each $R^4$ is individually a hydrocarbon group or PEG group; $R^5$ is the carbon chain of fatty acid; l is from about 1 to about 323; and n is from about 1 to about 370.

In a eleventh embodiment a polymer is provided as in any of the first through tenth embodiments, where the polymer is defined by the formula

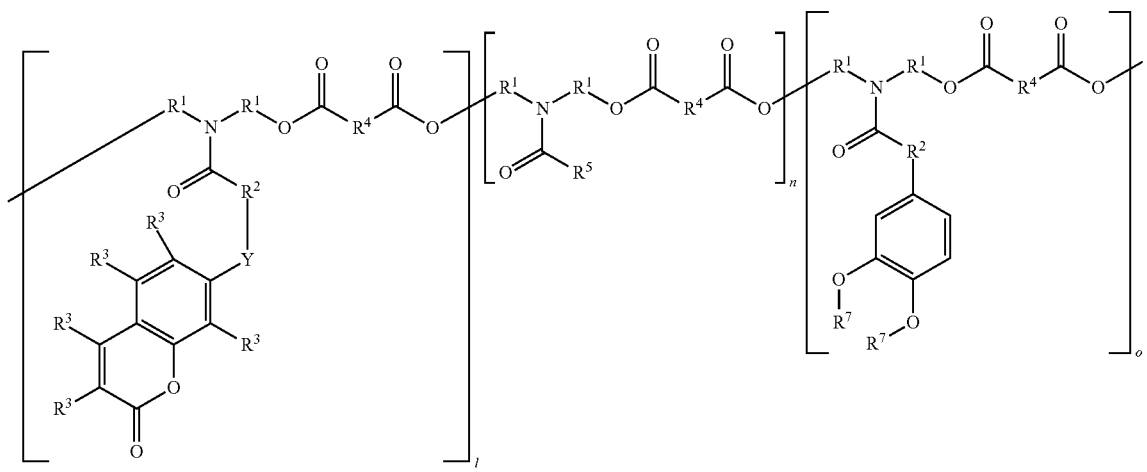

where each $R^1$ is individually a hydrocarbon group, each $R^2$ is individually a hydrocarbon group; each $R^3$ is individually a hydrogen atom, a halogen atom or an alkoxy group; Y is an oxygen atom or an amide group; each $R^4$ is individually a hydrocarbon group or PEG group; $R^5$ is the carbon chain of fatty acid; each $R^7$ is individually a hydrogen atom or an organic group, or where the two $R^7$ groups combine to make a single organic group; l is about 1 to about 100 units; n is about 2 to about 300 units; and o is about 1 to about 200 units.

In a twelfth embodiment a polymer is provided as in any of the first through eleventh embodiments, where the polymer is defined by the formula

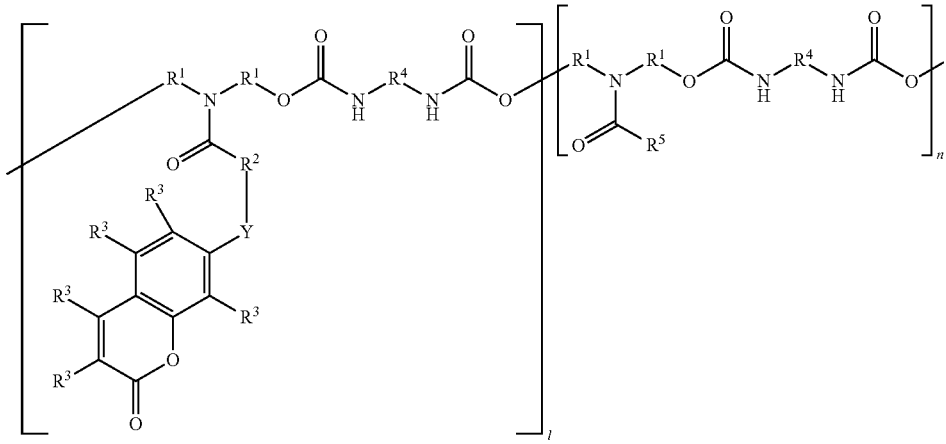

where each $R^1$ is individually a hydrocarbon group, $R^2$ is a hydrocarbon group; each $R^3$ is individually a hydrogen atom, a halogen atom or an alkoxy group; Y is an oxygen atom or an amide group; each $R^4$ is individually a hydrocarbon group or PEG group; $R^5$ is the carbon chain of fatty acid; l is from about 1 to about 323; and n is from about 1 to about 370.

In a thirteenth embodiment a polymer is provided as in any of the first through twelfth embodiments, where the polymer is defined by the formula

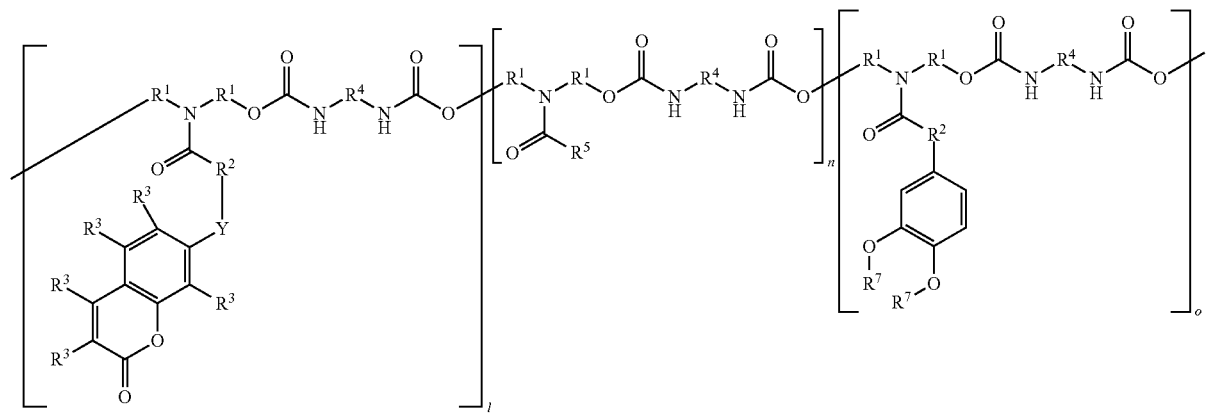

where each $R^1$ is individually a hydrocarbon group, each $R^2$ is individually a hydrocarbon group; each $R^3$ is individually a hydrogen atom, a halogen atom or an alkoxy group; Y is an oxygen atom or an amide group; each $R^4$ is individually a hydrocarbon group or PEG group; $R^5$ is the carbon chain of fatty acid; each $R^7$ is individually a hydrogen atom or an organic group, or where the two $R^7$ groups combine to make a single organic group; l is about 1 to about 100 units; n is about 2 to about 300 units; and o is about 1 to about 200 units.

In a fourteenth embodiment a polymer is provided as in any of the first through thirteenth embodiments, where the lap shear strength is greater than 300 kPa.

In a fifteenth embodiment a polymer is provided as in any of the first through fourteenth embodiments, where the lap shear strength is less than 10 kPa.

In a sixteenth embodiment a polymer is provided as in any of the first through fifteenth embodiments, where the polymer is a liquid.

In a seventeenth embodiment a polymer is provided as in any of the first through sixteenth embodiments, where the polymer is a solid.

In an eighteenth embodiment a polymer is provided as in any of the first through seventeenth embodiments, where the polymer further comprises a third unit derived from an amide functional diol compound that includes a polyethylene glycol chain.

In a nineteenth embodiment a polymer is provided as in any of the first through eighteenth embodiments, where the unit derived from an amide functional diol compound that includes a polyethylene glycol (PEG) chain may be defined by the formula

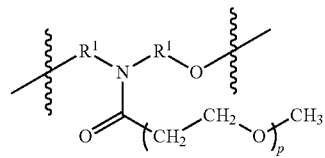

where each $R^1$ is individually a hydrocarbon group and p is from about 3 to about 30 units. In certain embodiments, p may be from about 8 to about 17 units.

In a twentieth embodiment a polymer is provided comprising a unit derived from an amide functional diol compound that includes a coumarin group; and a unit derived from an amide functional diol compound that includes a polyethylene glycol chain.

In a twenty-first embodiment, an adhesive article is provided comprising a substrate coated with the any of the previously described polymers.

In a twenty-second embodiment a monomer is provided, where the monomer is defined by the formula:

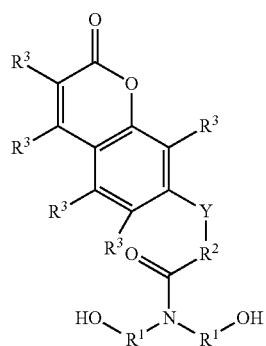

where each $R^1$ is individually a hydrocarbon group, $R^2$ is a hydrocarbon group; each $R^3$ is individually a hydrogen atom, a halogen atom or an alkoxy group, and Y is an oxygen atom or an amide group.

In a twenty-third embodiment a method of 3D printing a structure is provided, the method comprising depositing the a photoresponsive polymer from the nozzle of a 3D printer to a platform, where the rate of deposition is adjusted by irradiating the polymer with a UV light.

In a twenty-fourth embodiment a method is provided as in the twenty-third embodiment, where the photoresponsive polymer comprises a first unit derived from an amide functional diol compound that includes a coumarin group; and a second unit derived from an amide functional diol compound that includes a fatty acid chain.

In a twenty-fifth embodiment a method of 3D printing is provided comprising: printing a photoresponsive polymer comprising a first unit derived from an amide functional diol compound that includes a coumarin group; and a second unit selected from a unit derived from an amide functional diol compound that includes a fatty acid chain, a unit derived from an amide functional diol compound that includes a polyethylene glycol chain, a unit derived from a diol co-monomer, and combinations thereof; and irradiating the photoresponsive polymer with a UV light to crosslink the coumarin group.

In a twenty-sixth embodiment a method of 3D printing is provided as in the twenty-fifth embodiment, where the second unit is a diol co-monomer defined by the formula

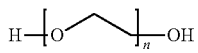

where n is from about 6 to about 250 units.

In a twenty-seventh embodiment, a method of 3D printing is provided as in the twenty-fifth embodiment or twenty-sixth embodiment, where the photoresponsive polymer further comprises a diacid defined by the formula

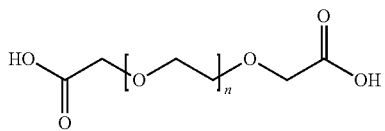

where n is from about 10 to about 15 units.

DETAILED DESCRIPTION OF ILLUSTRATIVE EMBODIMENTS

Figure 1:
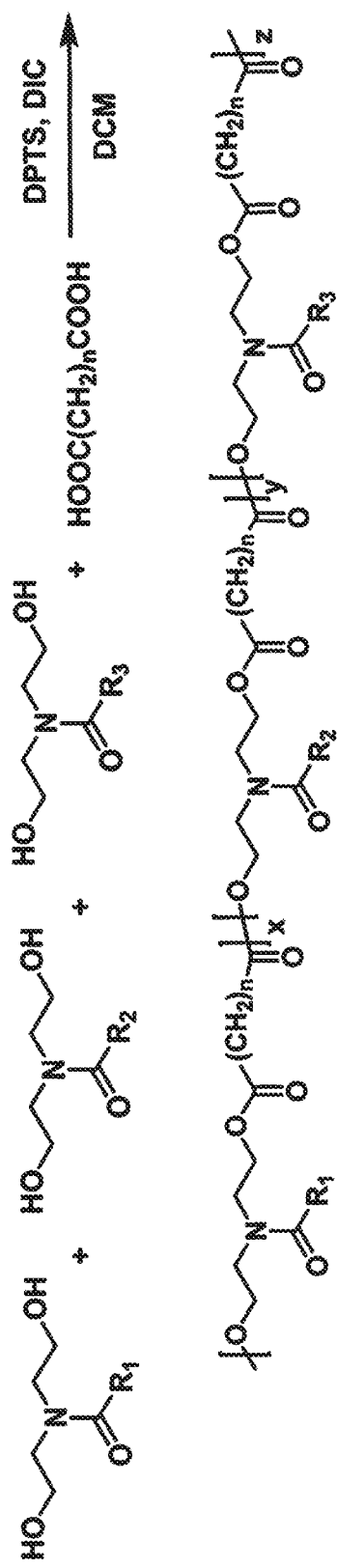
FIG. 1 provides a schematic of the synthesis of the polymers of one or more embodiments.
Figure 1:
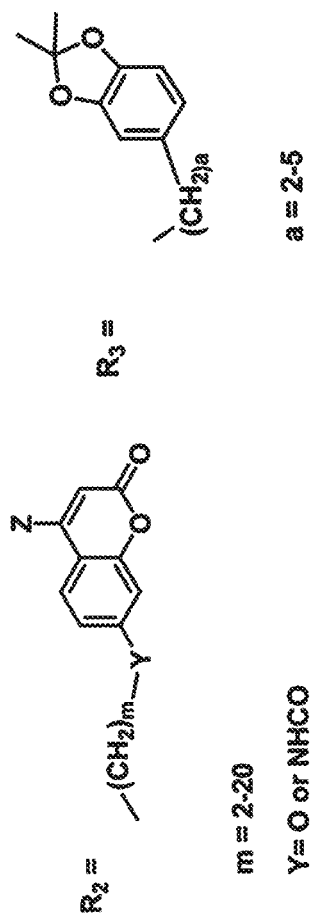
Figure 1:
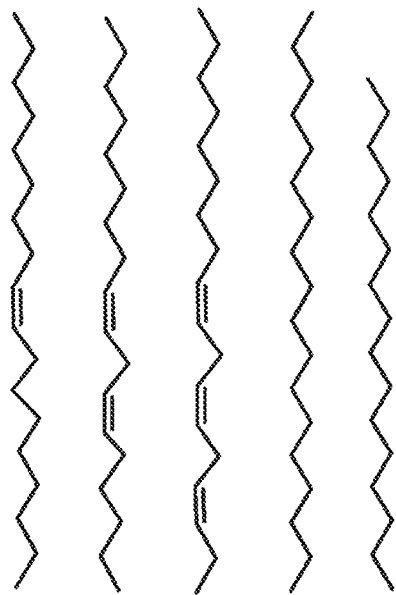
Figure 2A:
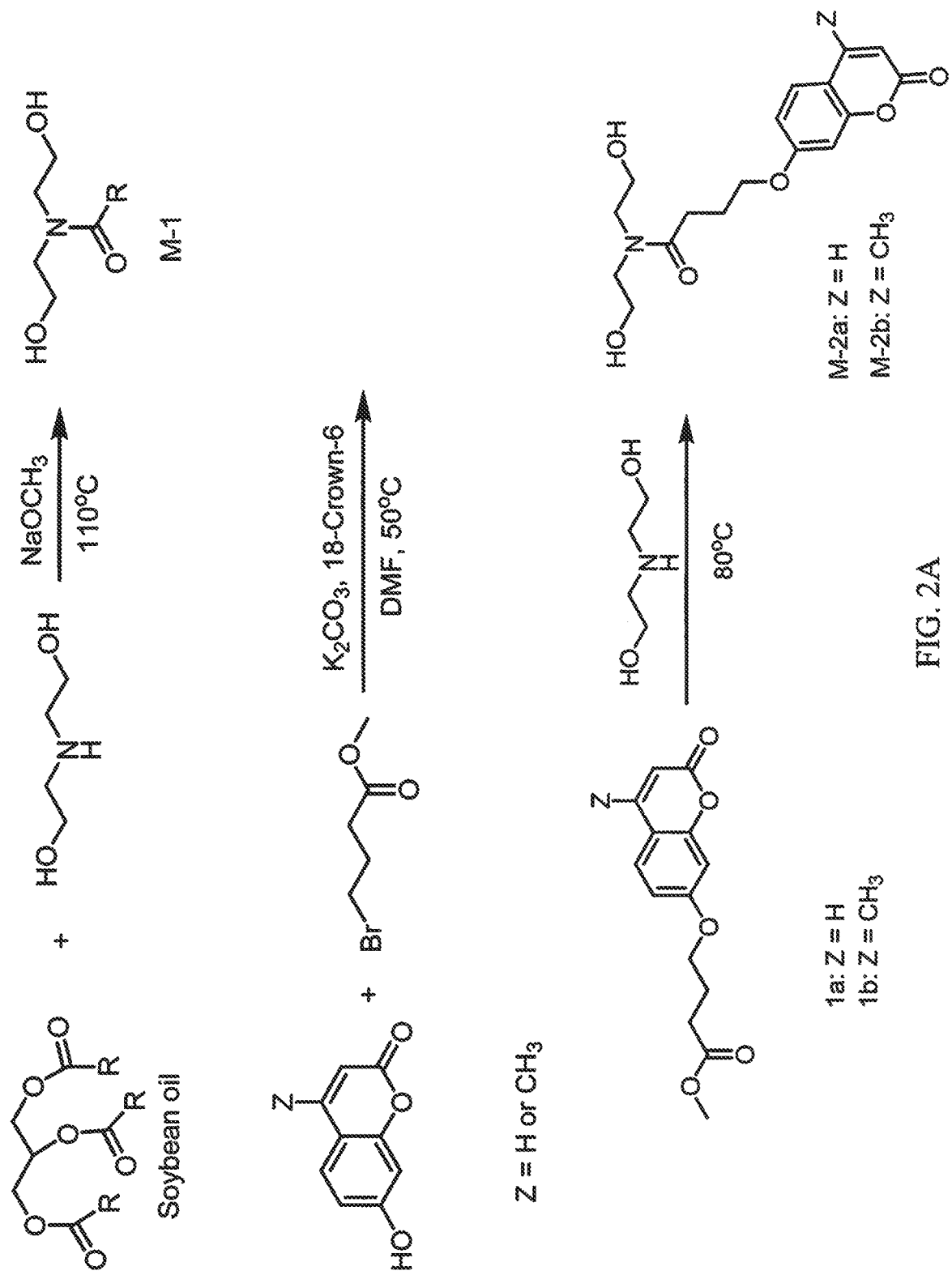
FIG. 2A provides a schematic of the synthesis of the monomers of one or more embodiments.
Figure 2B:
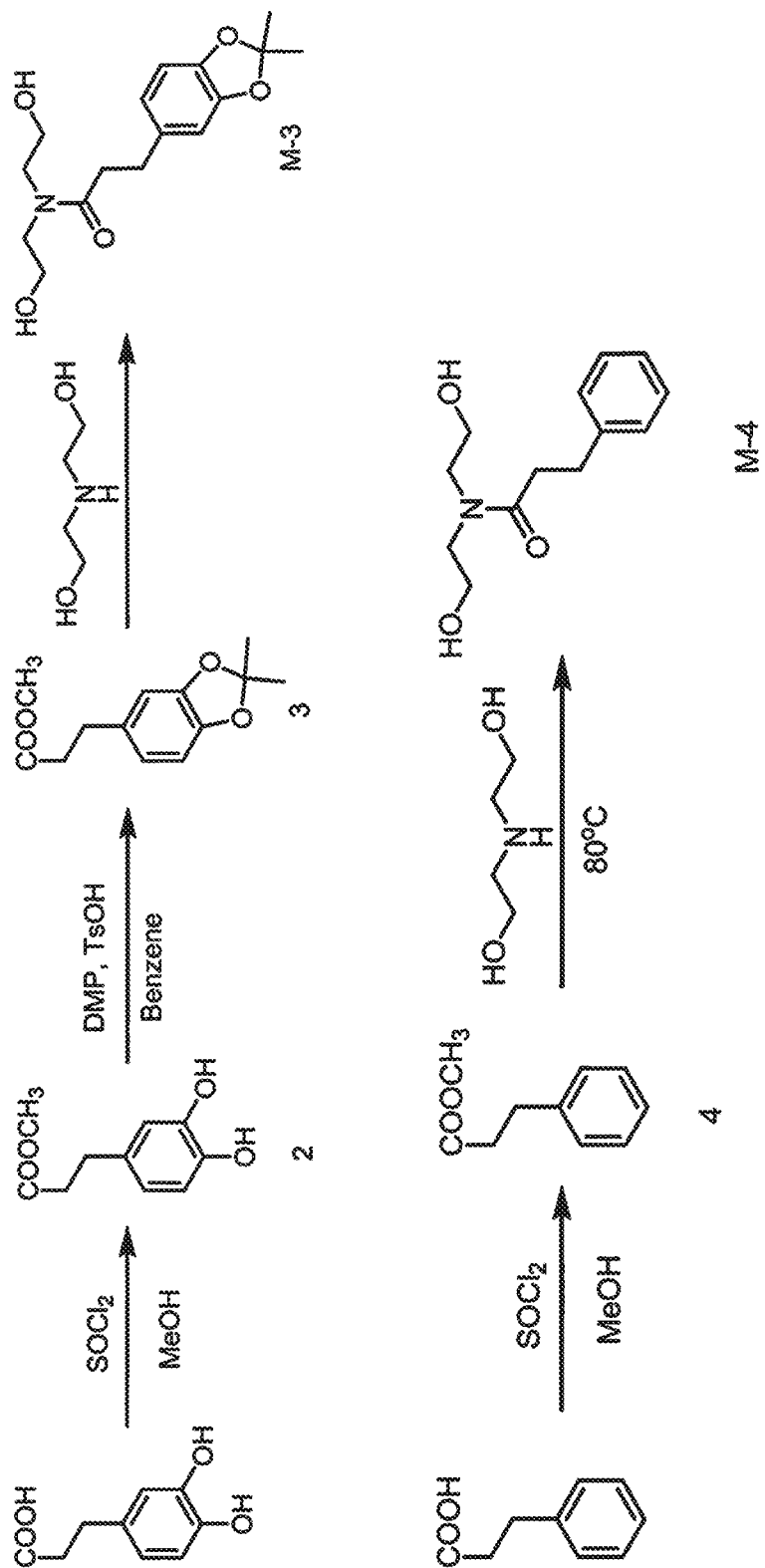
FIG. 2B provides a schematic of the synthesis of the monomers of one or more embodiments.
Figure 3A:
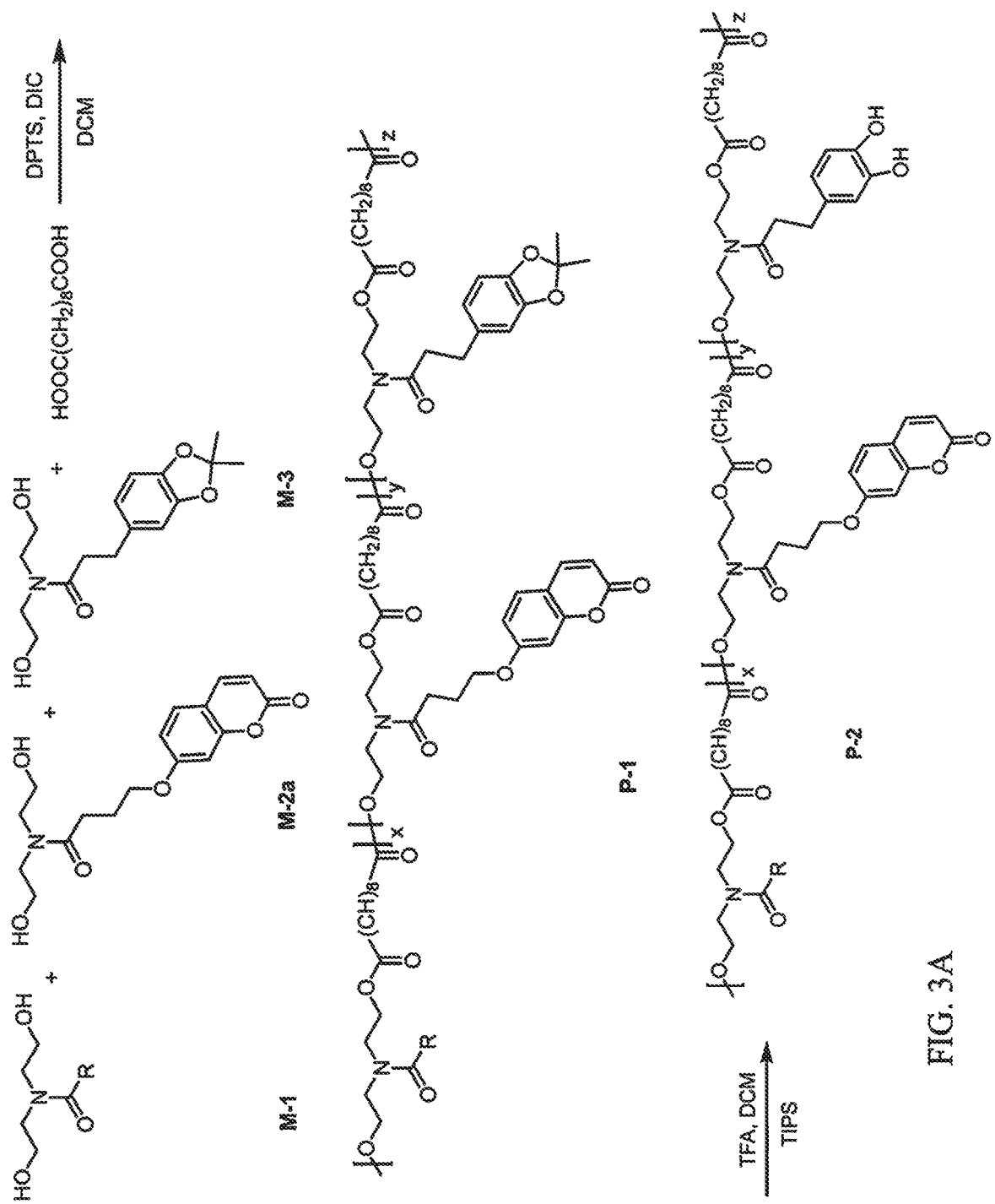
FIG. 3A provides a schematic of the synthesis of the polymers of one or more embodiments.
Figure 3B:
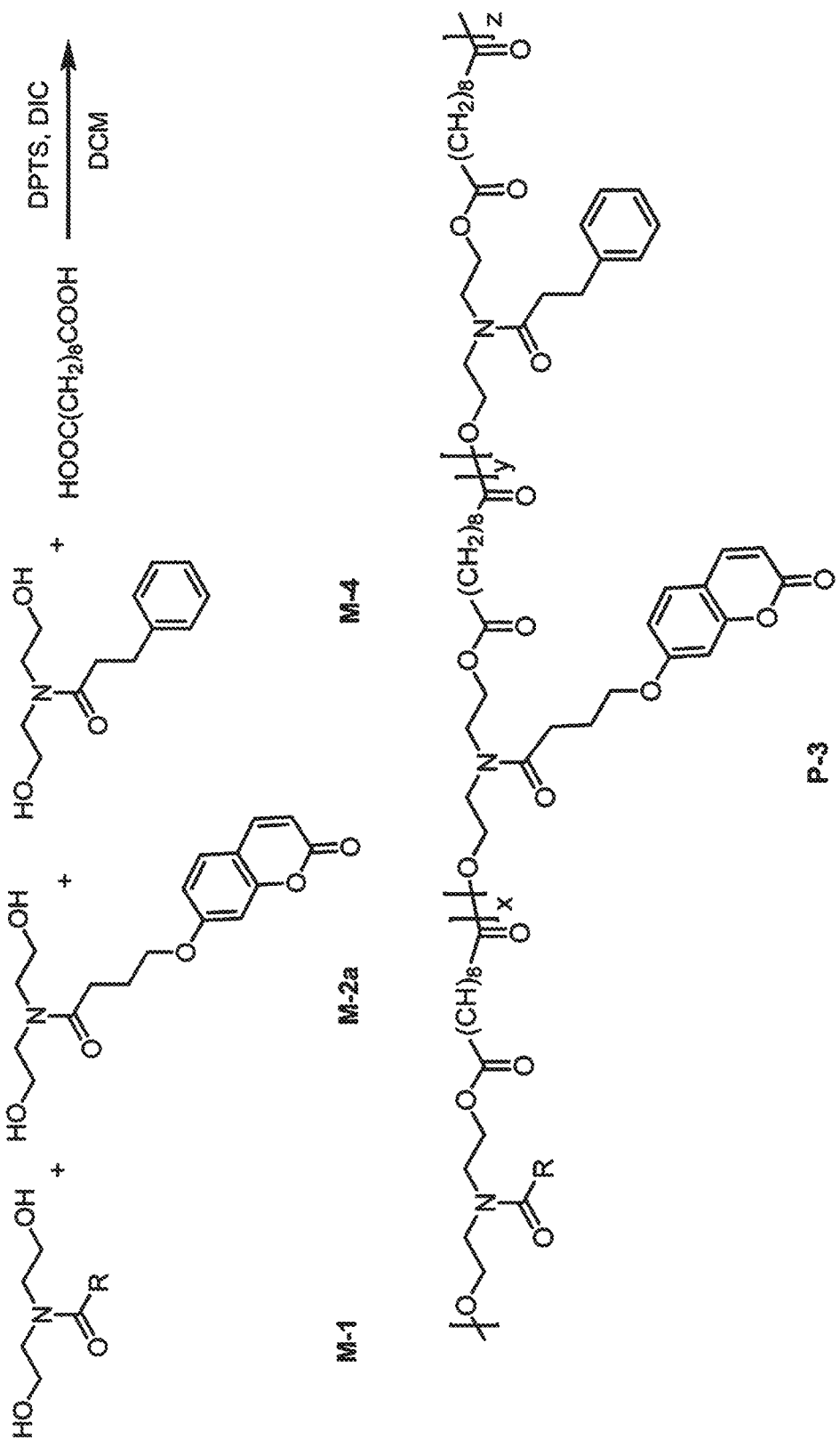
FIG. 3B provides a schematic of the synthesis of the polymers of one or more embodiments.
Figure 3C:
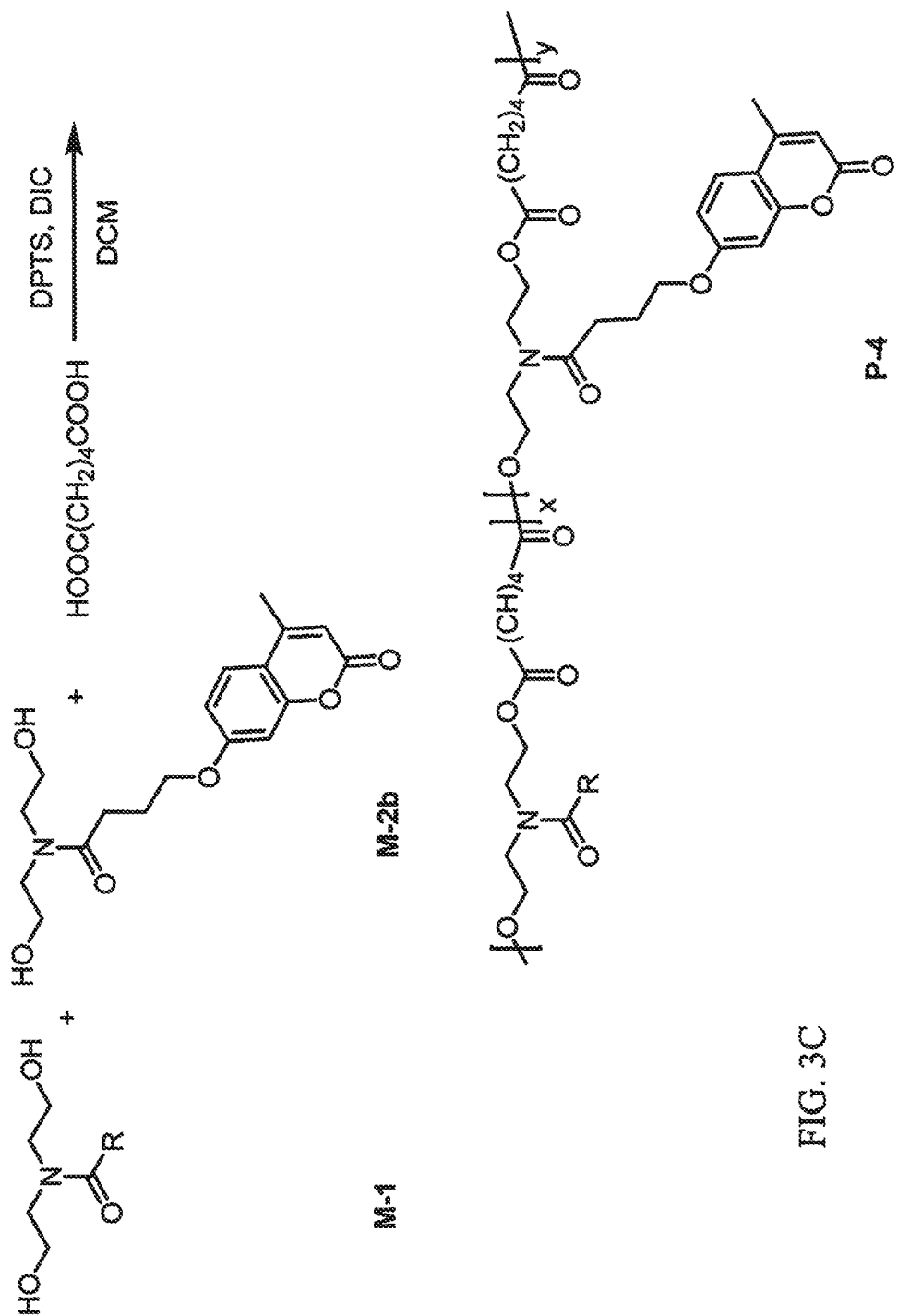
FIG. 3C provides a schematic of the synthesis of the polymers of one or more embodiments.
Figure 4A:
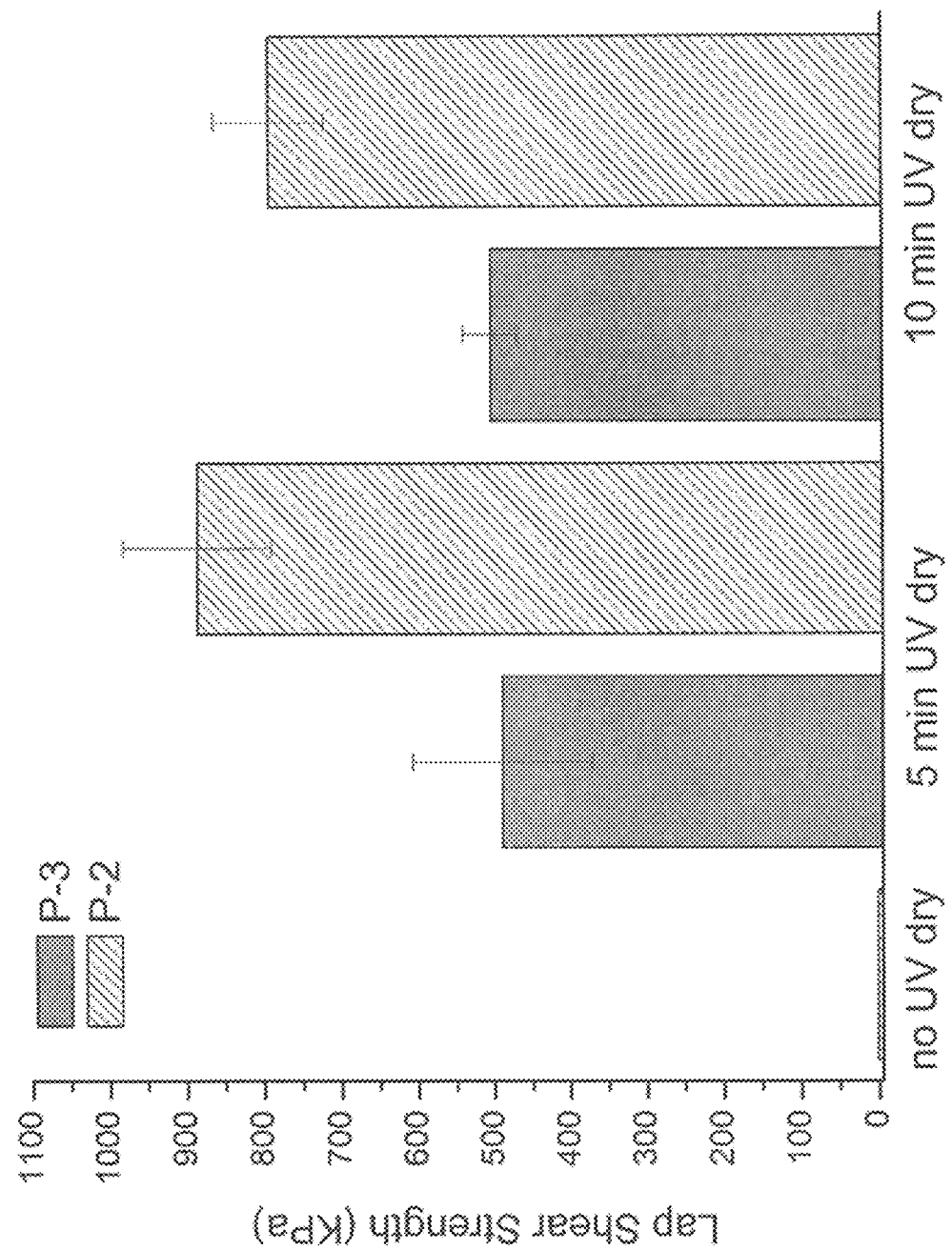
FIG. 4A provides a graph of the lap shear strengths of the polymers of one or more embodiments at after 0 minutes, 5 minutes and 10 minutes of exposure to UV irradiation.
Figure 4B:
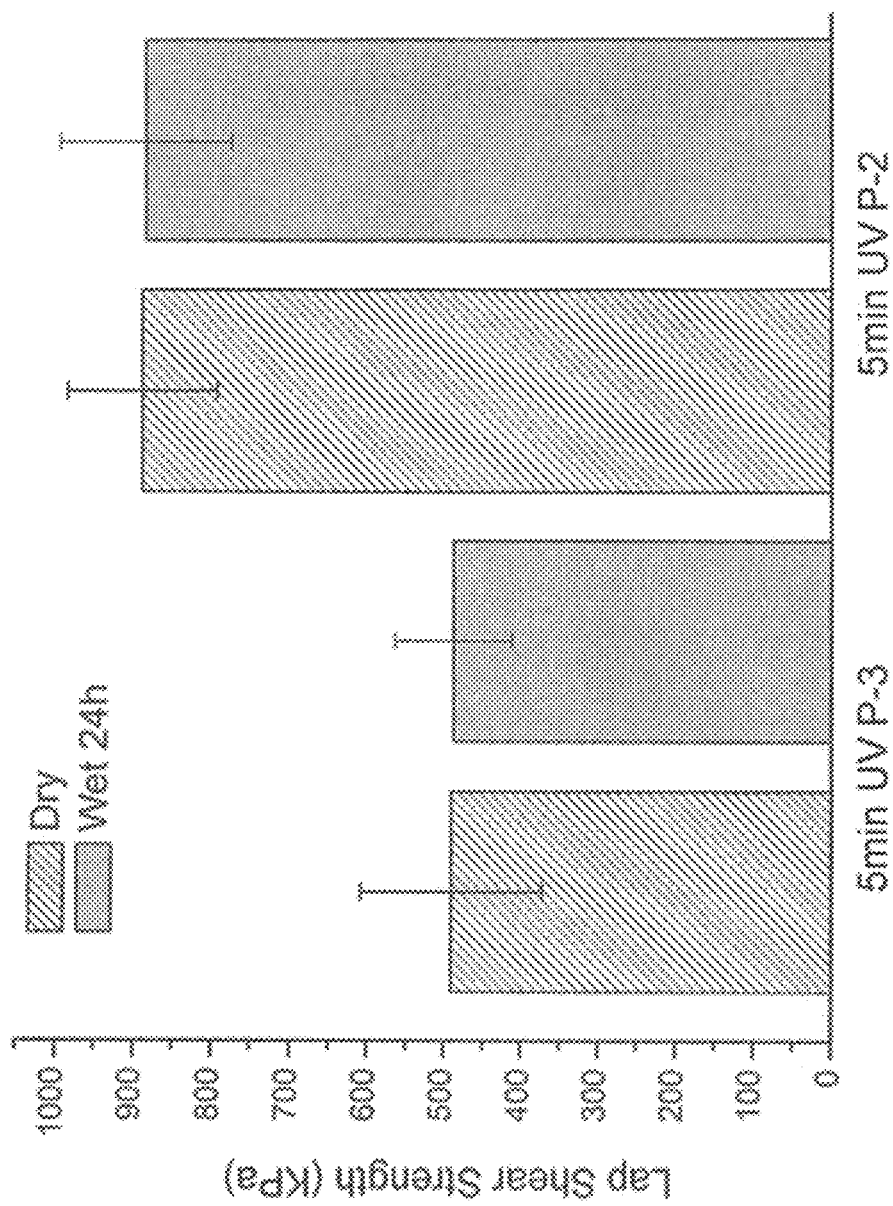
FIG. 4B provides a graph of the lap shear strengths of the polymers of one or more embodiments under wet and dry conditions after 5 minutes of exposure to UV irradiation.

Embodiments are based, at least in part, on the discovery that photoresponsive polymers may be prepared using amide functional diol compounds. For the purpose of the specification, the photoresponsive polymers prepared using amide functional diol compounds may simply be referred to as photoresponsive polymers. Advantageously, the photoresponsive groups of the photoresponsive polymers may be used to control the viscosity of the photoresponsive polymer. For example, a photoresponsive polymer may change from a viscoelastic polymer to an elastomeric solid when irradiated by crosslinking the photoresponsize groups. The photoresponsive polymer, when it is in an uncrosslinked state is a viscus liquid, upon crosslinking the photoresponsive polymer has properties similar to a thermoset elastomer. In certain embodiments, the photoresponsive polymers may include a group that provides adhesive properties to the polymer.

In one or more embodiments, an amide functional diol compound may be defined by the formula

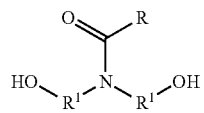

where each $R^1$ is individually a hydrocarbon group and R is a functional group. The R group may be selected to provide different functionalities in the photoresponsive polymer. Specific examples of amide functional diol compounds may be found in U.S. Pat. Pub. No. 2015/009442, which is incorporated herein by reference. Due to the diol functionality, an amide functional diol compound may be used as a monomer to produce polyesters, polyurethanes, or polycarbonates.

In one or more embodiments, the photoresponsive polymer may be prepared from an amide functional diol compound that includes a coumarin group. As used herein, the term "derived from" may be used to describe the portion of a polymer (i.e. mer unit) that results from the polymerization of a monomer. For example, the resulting polymer prepared from an amide functional diol compound that includes a coumarin group may be described as including a unit derived from an amide functional diol compound that includes a coumarin group.

Those skilled in the art will appreciate that a coumarin group may be defined by the following formula:

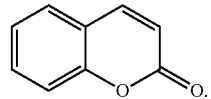

In one or more embodiments, the coumarin group may have a substitution at any of the hydrogen atoms of the base coumarin group. In these or other embodiments, the coumarin group may have one or more hydrogen atoms substituted with a bromine atom, an iodine atom, an alkyl or an alkoxy group.

Coumarin groups are useful in the production of photoresponsive polymers because they provide a reversible crosslink. Coumarin groups are capable of undergoing photodimerization with another coumarin group or form a crosslink with a double bond when the photoresponsive polymer is irradiated with light. In one or more embodiments, photoresponsive polymer with a coumarin group may undergo photodimerization when irradiated at a wavelength of about 320 nm to about 420 nm. The dimerization or crosslink may be reversed by the irradiation of a crosslinked polymer. In one or more embodiments, the dimer of coumarin group may separate when irradiated at a wavelength of about 230 nm to about 300 nm.

In one or more embodiments, the amide functional diol compound that includes a coumarin group may be defined by the formula:

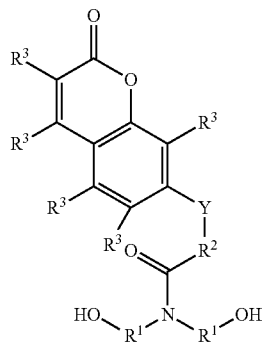

where each $R^1$ is individually a hydrocarbon group, $R^2$ is a hydrocarbon group; each $R^3$ is individually a hydrogen atom, a halogen atom or an alkoxy group, and Y is an oxygen atom or an amide group.

Specific examples of amide functional diol compounds that includes a coumarin group include

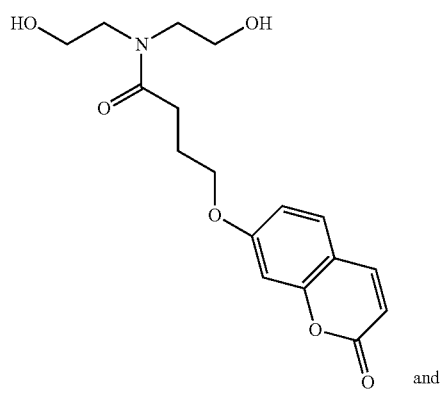

and

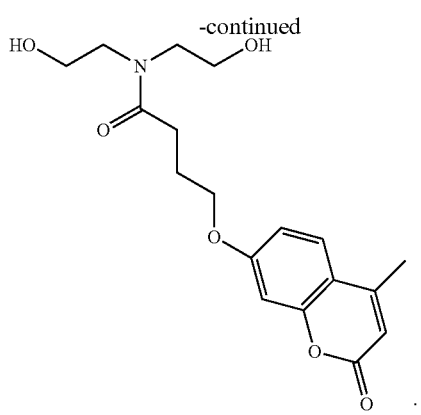

In one or more embodiments, the photoresponsive polymer may be prepared from an amide functional diol compound that includes a fatty acid chain. In these or other embodiments, the alkyl chain of the fatty acid is the pendant group of the amide functional diol. Those skilled in the art will recognize that a fatty acid is a carboxylic acid with a long aliphatic tail or chain, which may be either saturated or unsaturated.

In one or more embodiments, the fatty acid may be characterized by the number of carbon atoms in the carbon chain. In one or more embodiments, the fatty acid may include at least 6 carbon atoms, in other embodiments at least 8 carbon atoms, and in other embodiments at least 10 carbon atoms in the carbon chain. In one or more embodiments, the fatty acid may include at most 28 carbon atoms, in other embodiments at most 24 carbon atoms, and in other embodiments at most 18 carbon atoms in the carbon chain. In one or more embodiments, the fatty acid may include from about 6 to about 28 carbon atoms, in other embodiments at from about 8 to about 18 carbon atoms, and in other embodiments at from about 10 to about 14 carbon atoms in the carbon chain.

In one or more embodiments, the fatty acid may be characterized by the number of double bonds the carbon chain. In one or more embodiments, the fatty acid may include one double bond, in other embodiments two double bonds, in other embodiments 3 double bonds, and in other embodiments more than 3 double bonds. In one or more embodiments, the fatty acid does not include a double bond.

In one or more embodiments, the fatty acid may be obtained from a vegetable oil. Specific examples of suitable vegetable oils for obtaining fatty acid include, but are not limited to, linseed oil (HELA), soybean oil (HESA), rapeseed oil (HERA), *theobroma* oil (HETA), and coconut oil (HECA).

In one or more embodiments, the amide functional diol compound that includes a fatty acid chain may be defined by the formula

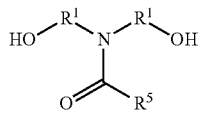

where each $R^1$ is individually a hydrocarbon group and $R^5$ is the carbon chain of fatty acid.

Specific examples of amide functional diol compounds that include a fatty acid chain may be selected from:

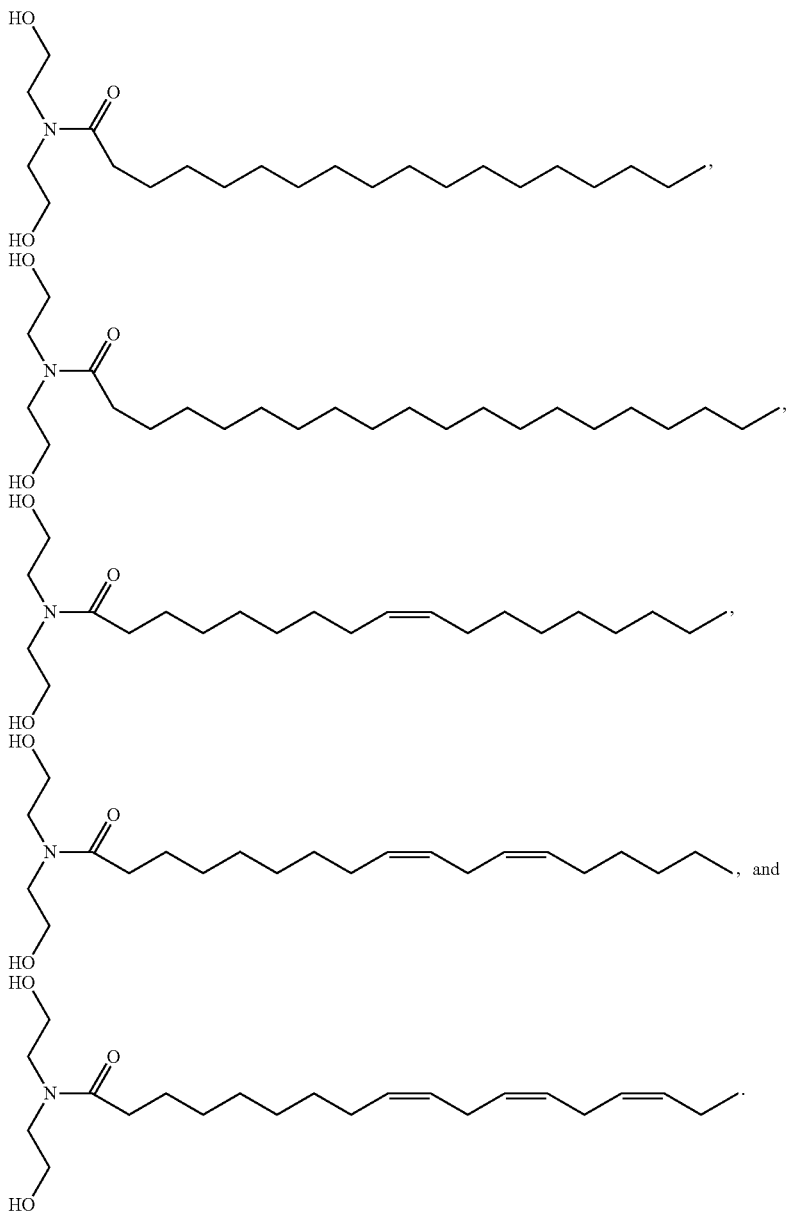

In one or more embodiments, the photoresponsive polymer may be prepared from an amide functional diol compound that includes a polyethylene glycol (PEG) chain. In one or more embodiments, the polyethylene glycol chain may be characterized by the number of repeating PEG units in the chain. In one or more embodiments, the polyethylene glycol chain may include at least 6 units, in other embodiments at least 10 units, and in other embodiments at least 25 units. In one or more embodiments, the fatty acid may include at most 20,000 units, in other embodiments at most 10,000 units, and in other embodiments at most 2,000 units. In one or more embodiments, the fatty acid may include from about 200 units to 20,000 units, in other embodiments at from about 400 units to 10,000 units, and in other embodiments at from about 1,000 units to 2,000 units.

In one or more embodiments, the amide functional diol compound that includes a polyethylene glycol (PEG) chain may be defined by the formula

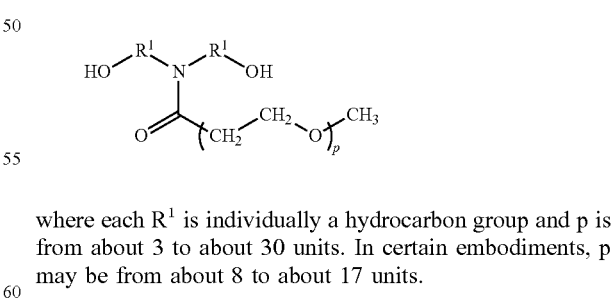

where each $R^1$ is individually a hydrocarbon group and p is from about 3 to about 30 units. In certain embodiments, p may be from about 8 to about 17 units.

As noted above, a photoresponsive polymer may include a group that provides adhesive properties to the polymer. Suitable groups for providing adhesive properties include catechol groups. In one or more embodiments, the photoresponsive polymer may be prepared from an amide functional diol compound that includes a catechol group or a protected catechol group.

Those skilled in the art will appreciate that a catechol group may be defined by the following formula:

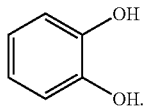

In one or more embodiments, the catechol group may have a substitution at any of the hydrogen atoms of the base catechol group. In these or other embodiments, the catechol group may have one or more hydrogen atoms substituted with a bromine atom, an iodine atom, an alkyl or an alkoxy group. In one or more embodiments, a hydrogen atom of the catechol group may be replaced with a protecting group. In these or other embodiments, the catechol group may be defined by the formula

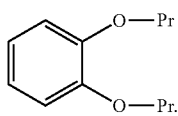

where each Pr is individually a protecting group or where the two Pr groups join to from on single divalent protecting group. Protecting groups are generally organic groups that may be removed to produce an alcohol group. Specific examples of protecting groups include methyl, acetonide, tetrahydropyran, and tert-butyldimethylsilyl.

In one or more embodiments, the amide functional diol compound that includes a catechol group or a protected catechol group may be defined by the following formula

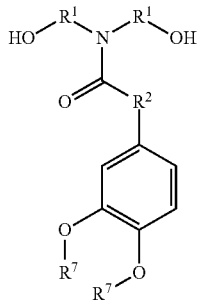

where each $R^1$ is individually a hydrocarbon group; $R^2$ is a hydrocarbon group; and each $R^7$ is individually a hydrogen atom or an organic group, or where the two $R^7$ groups combine to make a single organic group. In one or more embodiments, each $R^7$ is a protecting group.

Specific examples of amide functional diol compounds that include a catechol group or a protected catechol group may be selected from:

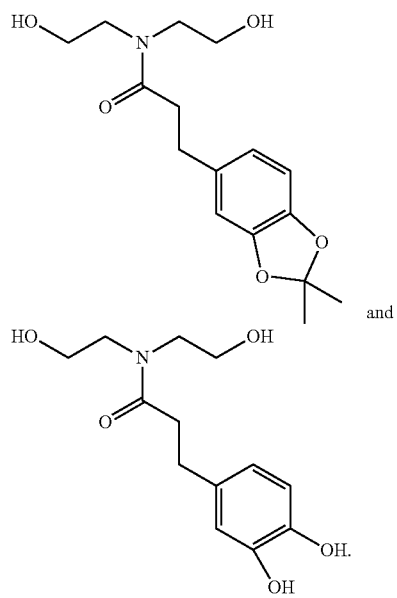

In one or more embodiments, one or more other diol compounds or diol co-monomers may be used along with the amide functional diol compounds to prepare a photoresponsive polymer. Suitable diols useful as co-monomers may be defined by the formula:

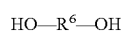

where $R^6$ is an organic group. In one or more embodiments, $R^6$ may be a hydrocarbon group with 1 to 10 carbon atoms. In other embodiments, $R^6$ may be a polyoxyethylene (i.e. $O-CH_2-CH_2)_n$ group. Suitable molecular weights of polyoxyethylene groups may be from 250 to 600 (n is 6-15 units), in other embodiments 400 to 1000 (n is 10-25 units), and in still other embodiments 2000 to 10000 (n is 50-250 units).

In one or more embodiments, where $R^6$ is a polyoxyethylene group, the diol may be defined by the formula

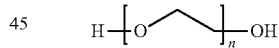

where n is from about 6 to about 250 units. In other embodiments, n may be from about 10 to about 25 unit, and in other embodiments from about 6 to about 15 units.

As noted above, amide functional diol compounds (and optionally a diol co-monomer) may be used to produce polyesters, polyurethanes, or polycarbonates. In these or other embodiments, the amide functional diol compounds (and optionally a diol co-monomer) are reacted with a co-monomer to produce a polymer. In one or more embodiments, where the amide functional diol compounds are used to prepare a polyester, the amide functional diol compounds (and optionally a diol co-monomer) may be reacted with a diacid. In one or more embodiments, where the amide functional diol compounds are used to prepare a polyurethane, the amide functional diol compounds (and optionally a diol co-monomer) may be reacted with a diisocyanate. In one or more embodiments, where the amide functional diol compounds are used to prepare a polycarbonate, the amide functional diol compounds (and optionally a diol co-monomer) may be reacted with phosgene.

In one or more embodiments, the comonomer is a diacid or diisocyanate defined by:

$$X^f\text{—}R^4\text{—}X^f$$

where $X^f$ is selected from carboxylic acid groups and isocyanate groups, and $R^4$ is a hydrocarbon or polyoxyethylene (PEG) group.

In one or more embodiments, where the $R^4$ group is a hydrocarbon group, group $R^4$ may be a linear, cyclic, or branched hydrocarbon group. In the case of dicarboxylic acid, the $R^4$ is a hydrocarbon group of from C2 to C8, in other embodiments, from C2 to C6, and in yet other embodiments C2 to C4. In the case of diisocyanates, the $R^4$ is a hydrocarbon group of from C6 to C10, in other embodiments, from C6 to C8, and in yet other embodiments C6. In other embodiments, where $R^4$ is a polyoxyethylene group, the molecular weight of polyoxyethylene groups may be from 440 and 600 (n is 8 to 14 units).

In one or more embodiments, where each $X^f$ is a carboxylic acid group, the comonomer is a dicarboxylic compound. Representative examples of dicarboxylic compounds suitable for use as a comonomer include, but are not limited to, succinic acid, glutaric acid, adipic acid, pimelic acid, and suberic acid.

In one or more embodiments, where $R^4$ is a polyoxyethylene group, the dicarboxylic compound may be defined by the formula

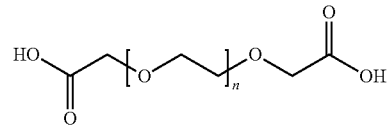

where n is from about 10 to about 15 units.

In one or more embodiments, where each $X^f$ is an isocyanate group, the comonomer is a diisocyanate compound. Representative examples of diisocyanate compounds suitable for use as a comonomer include, but are not limited to, hexamethylene diisocyanate and 1,3-phenylene diisocyanate.

In one or more embodiments, where $R^4$ is a polyoxyethylene group, the diisocyanate compound may be defined by the formula $$O\!=\!C\!=\!N\text{—}(CH_2CH_2O)n\text{-}CH_2CH_2\text{—}N\!=\!C\!=\!O$$

where n is from about 9 to about 14 units.

In one or more embodiments, where photoresponsive polymer is a polyester that includes a unit derived from an amide functional diol compound that includes a coumarin group, and unit derived from an amide functional diol compound that includes a fatty acid chain the polyester may be defined by the formula:

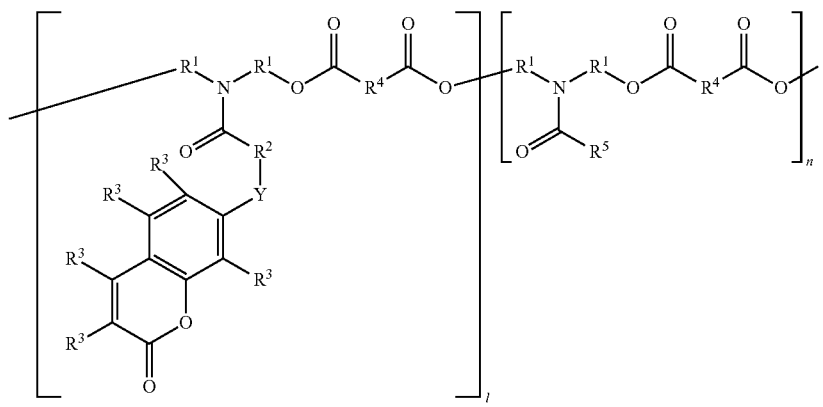

where each $R^1$ is individually a hydrocarbon group, $R^2$ is a hydrocarbon group; each $R^3$ is individually a hydrogen atom, a halogen atom or an alkoxy group; Y is an oxygen atom or an amide group; each $R^4$ is individually a hydrocarbon group or PEG group; $R^5$ is the carbon chain of fatty acid; l is from about 1 to about 323; and n is from about 1 to about 370. In one or more embodiments, l may be from about 1 to about 200 and in other embodiments from about 1 to about 100. In one or more embodiments, n may be from about 7 to about 400 and in other embodiments about 7 to about 200.

In one or more embodiments, where photoresponsive polymer is a polyester that includes a unit derived from an amide functional diol compound that includes a coumarin group, a unit derived from an amide functional diol compound that includes a fatty acid chain, and unit derived from an amide functional diol compound that includes catechol group or a protected catechol group the polyester may be defined by the formula:

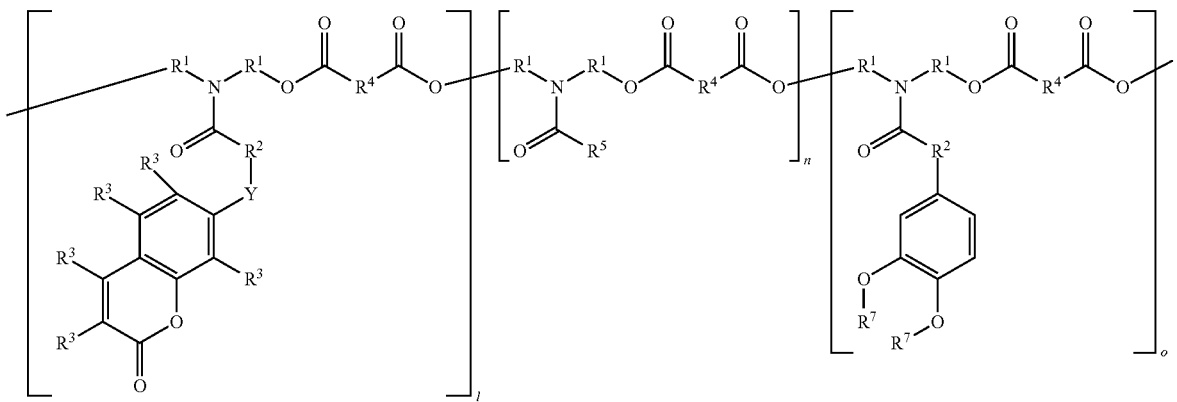

where each $R^1$ is individually a hydrocarbon group, each $R^2$ is individually a hydrocarbon group; each $R^3$ is individually a hydrogen atom, a halogen atom or an alkoxy group; Y is an oxygen atom or an amide group; each $R^4$ is individually a hydrocarbon group or PEG group; $R^5$ is the carbon chain of fatty acid; each $R^7$ is individually a hydrogen atom or an organic group, or where the two $R^7$ groups combine to make a single organic group; l is about 1 to about 100 units; n is about 2 to about 300 units; and o is about 1 to about 200 units. In these or other embodiments, l may be from about 1 to about 80 units, in other embodiments from 1 to about 20 units, and in other embodiments from 1 to about 10 units.

In these or other embodiments, n may be from about 2 to about 100 units, in other embodiments from 2 to about 50 units, and in other embodiments from 2 to about 25 units. In these or other embodiments, o may be from about 1 to about 50 units, in other embodiments from 1 to about 20 units, and in other embodiments from 1 to about 10 units.

In one or more embodiments, where photoresponsive polymer is a polyurethane that includes a unit derived from an amide functional diol compound that includes a coumarin group, and unit derived from an amide functional diol compound that includes a fatty acid chain the polyurethane may be defined by the formula:

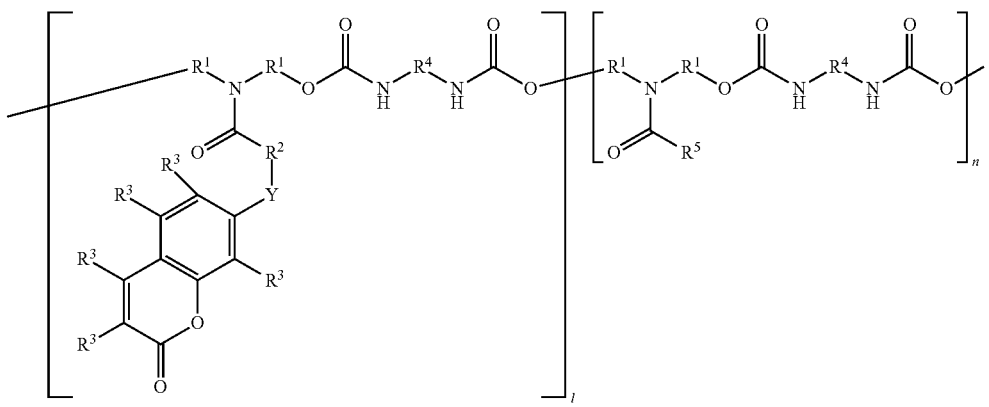

where each $R^1$ is individually a hydrocarbon group, $R^2$ is a hydrocarbon group; each $R^3$ is individually a hydrogen atom, a halogen atom or an alkoxy group; Y is an oxygen atom or an amide group; each $R^4$ is individually a hydrocarbon group or PEG group; $R^5$ is the carbon chain of fatty acid; l is from about 1 to about 323; and n is from about 1 to about 370. In one or more embodiments, l may be from about 1 to about 200 and in other embodiments from about 1 to about 100. In one or more embodiments, n may be from about 7 to about 400 and in other embodiments about 7 to about 200.

In one or more embodiments, where photoresponsive polymer is a polyurethane that includes a unit derived from an amide functional diol compound that includes a coumarin group, a unit derived from an amide functional diol compound that includes a fatty acid chain, and unit derived from an amide functional diol compound that includes catechol group or a protected catechol group the polyurethane may be defined by the formula:

bond between substrates in wet environments. Furthermore, the adhesive can be applied without any solvent and is therefore is an ideal biomedical adhesive. In these or other embodiments, the photoresponsive polymer may be used in an adhesive article, where the article comprises a substrate coated on at least one side with photoresponsive polymer. A substrate may refer to any item capable of having an adhesive surface.

Advantageously, the photoresponsive adhesive may be used as a single-component adhesive. Single-component adhesives are advantageous because they include a built in crosslinker. For certain uses, single-component adhesives are more convenient than multi-component adhesives, because adhesive and crosslinker of a multi-component adhesives must be stored separately. Additionally, quality control issues may arise from poorly mixed multi-component adhesives or multi-component adhesives that use incorrect ratios of components.

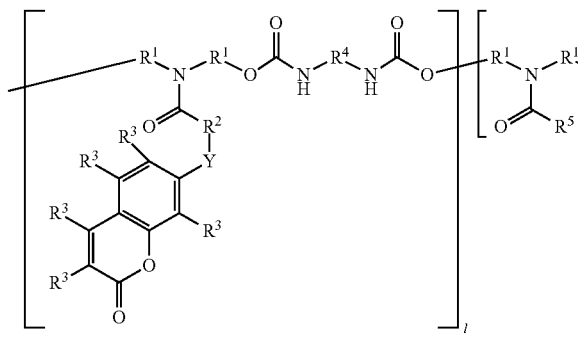 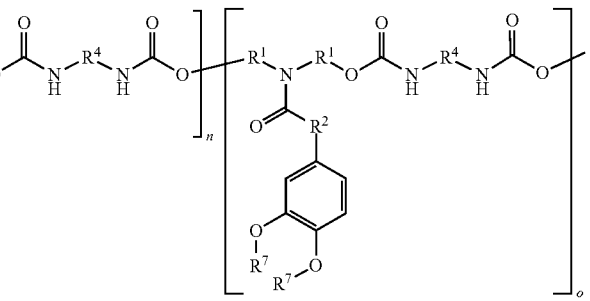

where each $R^1$ is individually a hydrocarbon group, each $R^2$ is individually a hydrocarbon group; each $R^3$ is individually a hydrogen atom, a halogen atom or an alkoxy group; Y is an oxygen atom or an amide group; each $R^4$ is individually a hydrocarbon group or PEG group; $R^5$ is the carbon chain of fatty acid; each $R^7$ is individually a hydrogen atom or an organic group, or where the two $R^7$ groups combine to make a single organic group; l is about 1 to about 100 units; n is about 2 to about 300 units; and o is about 1 to about 200 units. In these or other embodiments, l may be from about 1 to about 80 units, in other embodiments from 1 to about 20 units, and in other embodiments from 1 to about 10 units. In these or other embodiments, n may be from about 2 to about 100 units, in other embodiments from 2 to about 50 units, and in other embodiments from 2 to about 25 units. In these or other embodiments, o may be from about 1 to about 50 units, in other embodiments from 1 to about 20 units, and in other embodiments from 1 to about 10 units.

As noted above, the photoresponsive polymers may be used as part of a photoresponsive adhesive. In certain embodiments, the photoresponsive polymer is prepared from amide functional diol compound that include a fatty acid chain, a coumarin group and a catechol group. This polymer has the ability to function as an adhesive in dry and wet conditions. The viscoelastic nature of the polymer provides effective contact between substrates; the coumarin units provide cohesive strength upon photocrosslinking and the catechol units provide effective adhesive strength between the adhesive and substrate. The hydrophobic nature of the long chain alkyl from the fatty acid chain prevents water penetration into the adhesive and provides an effective In one or more embodiments, the photoresponsive adhesive may have a high adhesive strength conformation and a low adhesive strength conformation. In one or more embodiments, the high adhesive conformation is where the photoresponsive adhesive is crosslinked and in the low adhesive conformation the crosslinks are broken. The strength of the may be measured by a lap shear adhesion testing.

Lap shear adhesion may be determined using a universal testing machines, for example and Instron. An example test determination include using a cross head speed was of 1.3 mm/min. Pre-cleaned glass slides (75 mm×25 mm,) may be used as adherends. Polymer adhesive is then applied on the adherends. Another glass slide is then placed in a lap configuration. Then the sample is cured with UV irradiation (320-450 nm) for various time. Dry samples may be kept in atomosphere before test. Wet sampled may be kept in water for 24 hours before test. The wet samples may either prepared in air or under water. Testing may be performed at room temperature.

In one or more embodiments the high strength conformation is at least 20 times stronger, in other embodiments at least 30 times stronger, in other embodiments at least 40 times stronger, and in still other embodiments at least 50 times stronger than the low strength conformation. In one or more embodiments, the high strength conformation is at most 2000 times stronger, in other embodiments at most 1000 times stronger, in other embodiments at most 200 times stronger, and in still other embodiments at most 100 times stronger than the low strength conformation. In these or other embodiments, the high strength conformation from about 20 times to about 2000 times stronger, in other embodiments from about 30 times to about 1000 times stronger, in other embodiments from about 40 times to about 200 times stronger, and in still other embodiments from about 50 times to about 100 times stronger than the low strength conformation.

In one or more embodiments, the uncrosslinked photoresponsive polymer has a lap shear strength that is less than 50 kPa, in other embodiments less than 10 kPa, in other embodiments, less than 5 kPa. In one or more embodiments, the crosslinked photoresponsive polymer has a lap shear strength is greater than 300 kPa, in other embodiments greater than 400 kPa, in other embodiments, greater than 500 kPa.

Because the viscosity of photoresponsive polymers may be controlled with UV light, and can undergo shear thinning, they are suitable for us in 3D printing. 3D printing is an additive process, where successive portions or layers of a photoresponsive polymer may be laid down and irradiated to solidify. Because the photresponsive polymers may be applied as a single-component, they are particularly suitable for 3D printing biomedical applications due to prevention of small molecule leakage in a local environment.

In certain embodiments, a 3D structure may be obtained or designed, for example using computer assisted design (CAD) software and imported or stored into 3D printer software. Typically, the device, or 3D printer, has a platform that the first of which the first layer of the photoresponsve polymer may be deposited. Successive layers or portions of the photoresponsive polymer are deposited upon each other until the 3D structure is formed. Upon deposition onto a platform or layer of photoresponsve polymer the material is crosslinked using UV light. The duration of UV light drives the final mechanical and thermal properties of the resulting 3D printed structure. Maximum UV crosslinking (i.e. an amount of irradiation that provides complete or sufficiently complete crosslinking) drives thermoset elastomer-like thermal stability. As duration of UV crosslinking increases, the final modulus of the 3D printed structure increases in turn.

The printability is dependent upon initial molecular weight and stoichiometric composition of these materials. As the molecular weight increases, the viscosity and initial modulus of these materials increase in turn. As the stoichiometric ratio of coumarin diol to other amide functional diol increases, the viscosity and initial modulus of these materials increase in turn. The viscosity and initial modulus of these materials guide filament deformation over time, with higher viscosities and higher moduli preventing deformation of the filament over a set time period.

In one or more embodiments, a 3D structure may be printed by depositing a photoresponsive polymer from a nozzle of a 3D printer to a platform. In these or other embodiments, the rate of deposition is adjusted by irradiating the polymer with a UV light. In one or more embodiments, the rate of deposition may be increased by irradiating the photoresponsive polymer with a wavelength suitable to uncrosslink the photoresponsive groups. In other embodiments, the rate of deposition is may be increased by irradiating the photoresponsive polymer with a wavelength suitable to crosslink the photoresponsive groups. Due to the nature of photoresponsive polymers, this method of adjusting the rate of deposition is applicable to other crosslinkable photoresponsive polymers.

In order to demonstrate the practice of the present invention, the following examples have been prepared and tested. The examples should not, however, be viewed as limiting the scope of the invention. The claims will serve to define the invention.

EXAMPLES

Synthesis of Monomer-1 (M-1)

Diethanolamine (31.5 g, 0.3 mol) was taken in a 500 mL round bottom flask. Sodium methoxide (0.8 g, 14.8 mmol) was added and stirred at 110° C. until the sodium methoxide was dissolved. Soybean oil (43.6 g, 0.05 mol) was added dropwise through addition funnel in 30 min. After addition of soybean oil, vacuum was applied. The reaction was stirred for another 1 h at 110° C. After cooling, the mixture was diluted with ethyl acetate and washed with 15 wt % aqueous NaCl solution and purified by flash column chromatography with a 5% MeOH in $CH_2Cl_2$ to obtain 48 g of light yellow oily product with 87% yield. $^1$H NMR (500 MHz, CHLOROFORM-d) 5.30-5.41 (m, 2.88H), 3.77-3.85 (m, 5.5H), 3.43-3.59 (m, 4H), 2.76-2.81 (m, 1.29H), 2.39 (t, J=7.70 Hz, 2H), 1.99-2.07 (m, 3.38H), 1.57-1.71 (m, 2.11H), 1.26-1.39 (m, 17.94H), 0.98 (t, J=7.46 Hz, 0.21H), 0.87-0.91 (m, 2.76H).

Synthesis of Compound 1a

7-Hydroxycoumarin (3.0 g, 18.5 mmol), $K_2CO_3$ (5.12 g, 37.0 mmol) and 18-crown-6 (244 mg, 0.924 mmol) were added in a 100 mL bound bottom flask. 20 mL anhydrous DMF was added to the flask. Methyl 4-bromobutyrate (4.7 mL, 37.2 mmol) was added by syringe. The flask was covered with aluminum foil and the mixture was stirred at 50° C. for 24 h. Solid was filtered and solvent was removed by rotary evaporation. 30 mL $H_2O$ was added and extracted with EtOAc (30 mL×3), DCM (30 mL×3). The organic layer was dried over anhydrous $Na_2SO_4$. Solvent was removed by rotary evaporation and the solid was washed with hexane and dried under vacuum oven to yield light yellow solid (4.80 g, 99%). $^1$H NMR (500 MHz, CHLOROFORM-d) 7.63 (d, J=9.54 Hz, 1H), 7.37 (d, J=8.56 Hz, 1H), 6.70-6.91 (m, 2H), 6.26 (d, J=9.54 Hz, 1H), 4.09 (t, J=6.11 Hz, 2H), 3.71 (s, 3H), 2.55 (t, J=7.21 Hz, 2H), 2.14-2.19 (m, 2H).

Compound 1b was synthesized through the same procedure with a 95% yield.

Synthesis of Monomer-2a (M-2a)

Diethanol amine (8.0 g, 76 mmol) and 1a (4.94 g, 18.8 mmol) were added into 100 mL round bottom flask and stirred for 8 h at 80° C. The reaction mixture was purified by flush column chromatography with 10% MeOH in $CH_2Cl_2$ to obtain the pure product as white solid with a yield around 90%. $^1$H NMR (300 MHz, CHLOROFORM-d) 7.63 (d, J=9.37 Hz, 1H), 7.36 (d, J=8.49 Hz, 1H), 6.72-6.95 (m, 2H), 6.24 (d, J=9.37 Hz, 1H), 4.10 (t, J=6.00 Hz, 2H), 3.79-3.90 (m, 4H), 3.52-3.60 (m, 4H), 3.16 (br. s., 2H), 2.64 (t, J=7.03 Hz, 2H), 2.14-2.23 (m, 2H).

Monomer-2b (M-2b) was synthesized through the same procedure with a 90% yield. 1H NMR (300 MHz, CDCl3) δ7.50-7.47 (1H, d), 6.88-6.80 (2H, m), 6.12 (1H, s), 4.08-4.12 (2H, t), 3.80-3.88 (4H, d), 3.52-3.59 (4H, d), 3.24 (2H, s), 2.62-2.67 (2H, t), 2.39 (3H, s), 2.16-2.21 (2H, t).

Synthesis of Monomer-3 (M-3)

Diethanol amine (14.6 g, 138.9 mmol) and 3 (6.8 g, 34.7 mmol) were taken in a round bottom flask and heated at 75° C. overnight. Then this reaction mixture was purified by column chromatography with 5% MeOH in $CH_2Cl_2$ to yield 7.6 g light yellow solid (71%). $^1$H NMR (300 MHz, CHLOROFORM-d) δ 6.57-6.72 (m, 3H), 3.88 (q, J=5.27 Hz, 2H), 3.72 (q, J=5.27 Hz, 2H), 3.58 (t, J=4.98 Hz, 2H), 3.44 (t, J=4.98 Hz, 2H), 2.97 (t, J=4.39 Hz, 1H), 2.89 (t, J=7.76 Hz, 2H), 2.76 (t, J=5.71 Hz, 1H), 2.66 (t, J=7.76 Hz, 2H), 1.66 (s, 6H). $^{13}$C NMR (75 MHz, CHLOROFORM-d) δ 174.6, 147.4, 145.8, 134.2, 120.5, 117.6, 108.7, 108.0, 61.5, 60.8, 52.1, 50.6, 35.7, 31.2, 25.8.

Synthesis of Polymer-1 (P-1)

M-1 (5.39 g, 14.62 mmol, 0.8 eq.), M-2a (306.4 mg, 0.91 mmol, 0.05 eq.), M-3 (848 mg, 2.74 mmol, 0.15 eq.), sebacic acid (3.696 g, 18.27 mmol, 1.0 eq.) and DPTS (2.137 g, 7.31 mmol, 0.4 eq.) were added to a 100 mL Schlenk flask. 20 mL anhydrous DCM was added to the flask under N2. This mixture was warmed up to 40° C. for 1-2 min and then cooled with ice bath. To this cooled mixture DIC (8.7 mL, 54.8 mmol, 3.0 eq.) was added dropwise and reaction mixture was stirred at room temperature for 48 h. Polymer was precipitated twice from methanol and dried under vacuum oven. $^{1}$H NMR (500 MHz, CHLOROFORM-d) 7.63 (d, J=9.29 Hz, 0.05H), 7.36 (d, J=8.56 Hz, 0.05H), 6.82-6.85 (m, 0.10H), 6.59-6.63 (m, 0.43H), 6.24 (d, J=9.54 Hz, 0.05H), 5.30-5.40 (m, 2.26H), 4.09-4.21 (m, 4H), 3.52-3.66 (m, 4H), 2.86 (t, J=7.83 Hz, 0.32H), 2.75-2.80 (m, 1.03H), 2.57-2.62 (m, 0.42H), 2.24-2.35 (m, 5.65H), 2.14-2.20 (m, 0.19H), 2.00-2.09 (m, 2.68H), 1.59-1.65 (m, 6.81H), 1.25-1.38 (m, 22.25H), 0.97 (t, J=7.46 Hz, 0.19H), 0.86-0.90 (m, 2.18H).

Synthesis of Polymer-2 (P-2)

P-1 (800 mg) and triisopropylsilane (50 μL) were dissolved in 5 mL DCM (degassed for 30 min). 5 mL TFA was added and the solution was stirred at r.t. for 2 h under N2. Solvent was removed by rotary evaporation. The polymer was precipitated from MeOH and dried under vacuum oven. $^{1}$H NMR (500 MHz, CHLOROFORM-d) 7.64 (d, J=9.54 Hz, 0.05H), 7.37 (d, J=8.56 Hz, 0.05H), 6.73-6.85 (m, 0.39H), 6.58 (d, J=7.34 Hz, 0.14H), 6.25 (d, J=9.29 Hz, 0.05H), 5.30-5.41 (m, 2.24H), 4.09-4.22 (m, 4H), 3.52-3.67 (m, 4H), 2.76-2.85 (m, 1.26H), 2.57-2.62 (m, 0.39H), 2.24-2.37 (m, 5.76H), 2.14-2.20 (m, 0.16H), 2.01-2.07 (m, 2.60H), 1.60 (s, br, 5.93H), 1.25-1.38 (m, 23.63H), 0.97 (t, J=7.46 Hz, 0.17H), 0.86-0.90 (m, 2.25H).

Synthesis of Polymer-3 (P-3)

M-1 (5.8303 g, 15.81 mmol, 0.8 eq.), M-2a (331.4 mg, 0.99 mmol, 0.05 eq.), M-4 (703.6 mg, 2.97 mmol, 0.15 eq.), sebacic acid (3.998 g, 19.77 mmol, 1.0 eq.) and DPTS (2.311 g, 7.91 mmol, 0.4 eq.) were added to a 100 Schlenk flask. 20 mL anhydrous DCM was added to the flask under N2. This mixture was warmed up to 40° C. for 1-2 min and then cooled with ice bath. To this cooled mixture DIC (9.3 mL, 59.31 mmol, 3.0 eq.) was added dropwise and reaction mixture was stirred at room temperature for 39 h. Polymer was precipitated twice from methanol and dried under vacuum oven. $^{1}$H NMR (500 MHz, CHLOROFORM-d) 7.63 (d, J=9.29 Hz, 0.05H), 7.37 (d, J=8.31 Hz, 0.05H), 7.18-7.30 (m, 1.11H), 6.82-6.85 (m, 0.10H), 6.24 (d, J=9.29 Hz, 0.05H), 5.30-5.41 (m, 2.21H), 4.09-4.22 (m, 4H), 3.51-3.67 (m, 4H), 2.98 (t, J=7.71 Hz, 0.29H), 2.76-2.81 (m, 0.99H), 2.67 (t, J=7.71 Hz, 0.29H), 2.59 (t, J=7.09 Hz, 0.10H), 2.17-2.36 (m, 5.70H), 2.01-2.10 (m, 2.59H), 1.61 (d, J=6.85 Hz, 2.68H), 1.26-1.39 (m, 21.93H), 0.98 (t, J=7.58 Hz, 0.16H), 0.87-0.91 (m, 2.13H).

Synthesis of Polymer-4 (P-4a, P-4b, P-4c)

TABLE 1

| | P-4 monomer measurements | | |
|---|---|---|---|
| Compound | Grams P-4a, P-4b, P-4c | mmol P-4a, P-4b, P-4c | Equivalents P-4a, P-4b, P-4c |
| M-1 | 3.015, 2.501, 2.012 | 8.218, 6.816, 5.484 | 0.6, 0.5, 0.4 |
| M-2b | 1.917, 2.386, 2.879 | 5.486, 6.828, 8.241 | 0.4, 0.5, 0.6 |
| Adipic Acid | 2.003, 1.994, 2.006 | 13.704, 13.644, 13.725 | 1, 1, 1 |
| DPTS | 1.612, 1.605, 1.615 | 5.481, 5.458, 5.490 | 0.4, 0.4, 0.4 |
| DIC | 5.188, 5.166, 5.196 | 41.111, 40.932, 41.174 | 3, 3, 3 |

M-1, M-2b, adipic acid and DPTS were added to a 250 mL Schlenk flask in amounts detailed in Table 1. 16 mL anhydrous DCM was added to the flask under N2. This mixture was warmed up to 45° C. for 1-2 min and then cooled with ice bath. To this cooled mixture DIC (Table 1 measurements) was added dropwise and reaction mixture was stirred at room temperature for 58 h. Polymer was precipitated twice from methanol and dried under vacuum oven.

P-4a 1H NMR (300 MHz, CDCl3) δ7.52-7.49 (0.4H, d), 6.88-6.82 (0.8H, t), 6.12 (0.3H, s), 5.36-5.34 (1.4H, d), 4.21-4.11 (4H, m), 3.62-3.60 (4H, d), 2.79-2.75 (0.6H, t), 2.62-2.57 (0.6H, t), 2.40-2.32 (6H, d), 2.19-2.15 (0.8H, t), 2.06-2.02 (1.80, t), 1.64-1.58 (6H, d), 1.32-1.26 (9.2H, d), 0.89 (1.5, s)

P-4b 1H NMR (300 MHz, CDCl3) δ7.52-7.49 (0.5H, d), 6.88-6.82 (1H, t), 6.12 (0.4H, s), 5.36-5.34 (1.3H, d), 4.21-4.11 (4H, m), 3.62-3.60 (4H, d), 2.79-2.75 (0.6H, t), 2.62-2.57 (0.9H, t), 2.40-2.31 (6H, d), 2.19-2.15 (1H, t), 2.06-2.02 (1.60, t), 1.63-1.58 (5.7H, d), 1.32-1.26 (7.9H, d), 0.89 (1.15, s)

P-4c 1H NMR (300 MHz, CDCl3) δ7.52-7.49 (0.6H, d), 6.88-6.82 (1.2H, t), 6.12 (0.5H, s), 5.36-5.34 (1H, d), 4.21-4.11 (4.6H, m), 3.62-3.60 (3.5H, d), 2.79-2.75 (0.5H, t), 2.62-2.57 (1.2H, t), 2.39-2.31 (5.8H, d), 2.19-2.15 (1.2H, t), 2.06-2.02 (1.2H, t), 1.63-1.58 (5.3H, d), 1.32-1.26 (5.8H, d), 0.89 (0.90, s)

Characterization of Polymers

| Polymer | Mn (kDa) | Mw (kDa) | PDI | Tg (° C.) | Td (° C.) |
|---|---|---|---|---|---|
| P-1 | 20 | 37 | 1.80 | −50.9 | 263.5 |
| P-3 | 20 | 34 | 1.65 | −52.1 | 309.3 |
| P-4a | 17.4 | 24.4 | 1.40 | | |
| P-4b | 11.3 | 14.7 | 1.30 | | |
| P-4c | 12.6 | 17.2 | 1.36 | | |

Lap Shear Test of Polymers

Micro slides with dimension of 25×75 mm and 1.0 mm thick were cleaned by immersing for 30 min in base bath, rinsing with water and drying with compressed air. Polymer was applied on the end of one slide with area of 25×12.5 mm$^2$ with spatula. Then the other slide was with a lap configuration. For the dry measurement, the specimens were tested with instron 30 min after UV irradiation. For the wet measurement, the specimen were immersed in water for 24 h after UV irradiation and then tested with instron immediately from water. The specimens were irradiated by Dymax.

The UV intensity from the tip of light guide was 5.0 w/cm$^2$ and the distance from tip to specimen was 5.3 cm. The load cell of instron was 1000N and the pulling rate was 1.3 mm/min. The strength was calculated as the maximum force divided by area. For each test, at least 5 samples were measured and averaged.

Both polymers have very low lap shear strength without UV irradiation at dry condition. P-2 showed 1.5±0.3 kPa with adhesive failure. After 5 min UV irradiation, coumarin pendent can undergo cross linking through [2+2] cyclization, the lap shear strength increased significantly for both polymers. Polymer with catechol group P-2 increased to 887±96 kPa while polymer with phenyl group P-3 increased to 490±117 kPa. The two polymers have similar failure which is a mix of adhesive and cohesive failure. When UV irradiation time was increased to 10 min, the lap shear strength of P-2 decreased slightly to 793±72 kPa and P-3 increased slightly to 505±35 kPa. The adhesion strength of both polymers with 5 min UV irradiation under wet condition was also tested. The lap shear strength was almost the same after immersing the samples for 24 h in water. It was 883±109 kPa for P-2 and 487±76 kPa for P-3.

Various modifications and alterations that do not depart from the scope and spirit of this invention will become apparent to those skilled in the art. This invention is not to be duly limited to the illustrative embodiments set forth herein.

What is claimed is:

1. A viscoelastic polymer comprising the formula

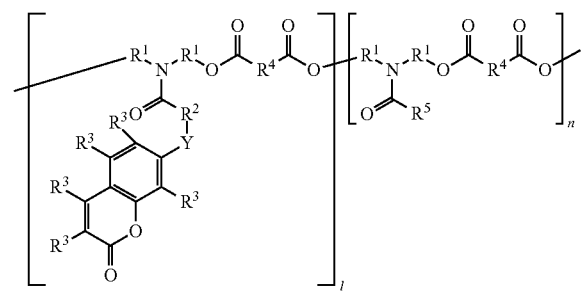

or

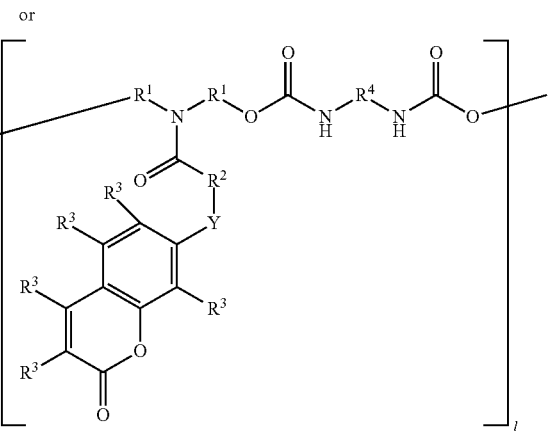

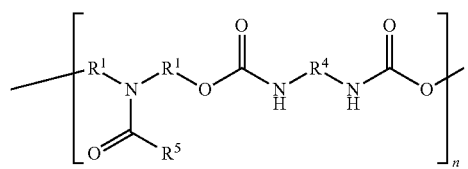

where each $R^1$ is individually a hydrocarbon group, $R^2$ is a hydrocarbon group; each $R^3$ is individually a hydrogen atom, a halogen atom or an alkoxy group; Y is an oxygen atom or an amide group; each $R^4$ is individually a hydrocarbon group or polyoxyethylene group having a molecular weight of from about 440 to about 600; $R^5$ is a saturated or unsaturated aliphatic hydrocarbon chain having from 6 to 28 carbon atoms in the chain; l is from about 1 to about 323; and n is from about 1 to about 400.

2. The polymer of claim 1, further comprising at least one unit derived from an amide functional diol compound that includes a catechol group, wherein the polymer is defined by the formula

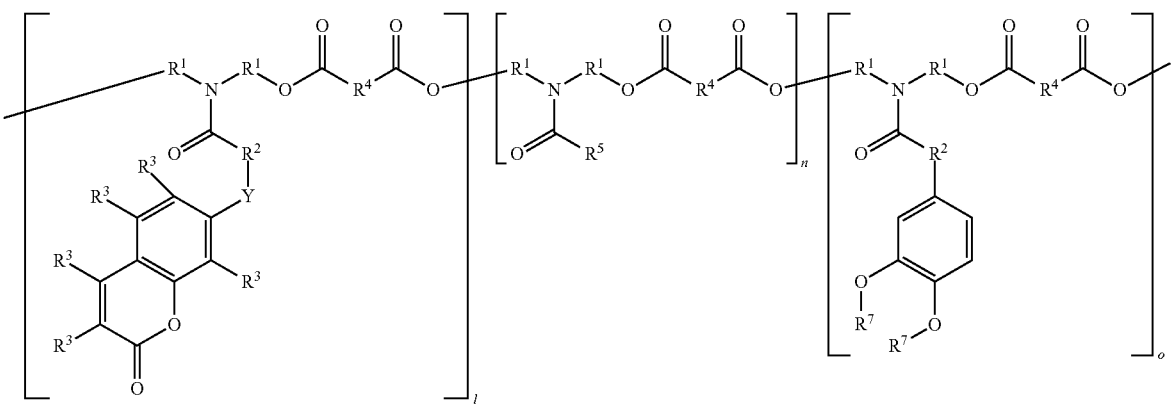

or

-continued

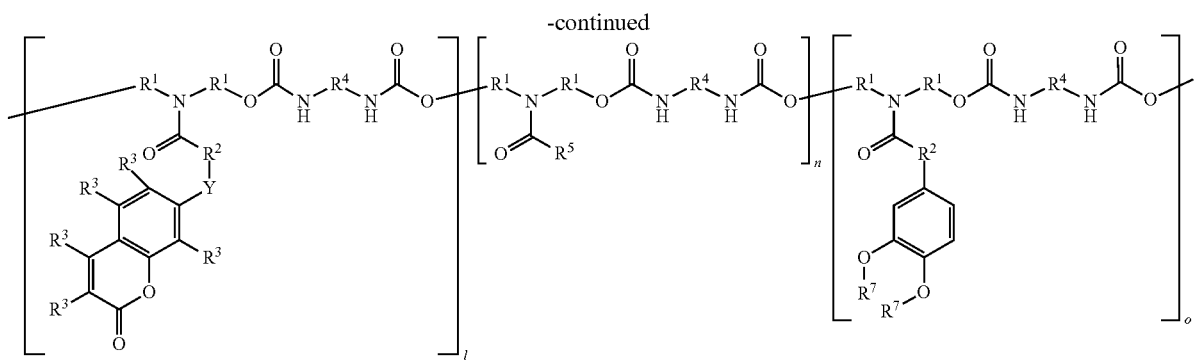

where each $R^1$ is individually a hydrocarbon group, $R^2$ is a hydrocarbon group; each $R^3$ is individually a hydrogen atom, a halogen atom or an alkoxy group, and Y is an oxygen atom or an amide group; each $R^4$ is individually a hydrocarbon group or polyoxyethylene group having a molecular weight of from about 440 to about 600; $R^5$ is a saturated or unsaturated aliphatic hydrocarbon chain having from 6 to 28 carbon atoms in the chain; each $R^7$ is individually a hydrogen atom or an organic group, or where the two $R^7$ groups combine to make a single organic group; l is about 1 to about 100 units; n is about 2 to about 300 units; and o is about 1 to about 200 units.

3. The polymer of claim 1, where the lap shear strength is greater than 300 kPa.

4. The polymer of claim 1, where the lap shear strength is less than 10 kPa.

5. The polymer of claim 1, where the polymer is a liquid.

6. The polymer of claim 1, where the polymer is a solid.

7. The polymer of claim 1, where the polymer further includes a unit defined by the formula

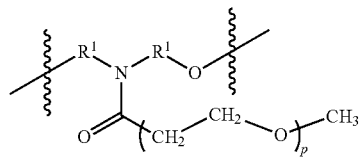

where each $R^1$ is individually a hydrocarbon group and p is from about 3 to about 30 units.

8. The polymer of claim 1, where l is from about 1 to about 200; and n is from about 7 to about 200.

9. The polymer of claim 1, where $R^5$ is selected from the group consisting of

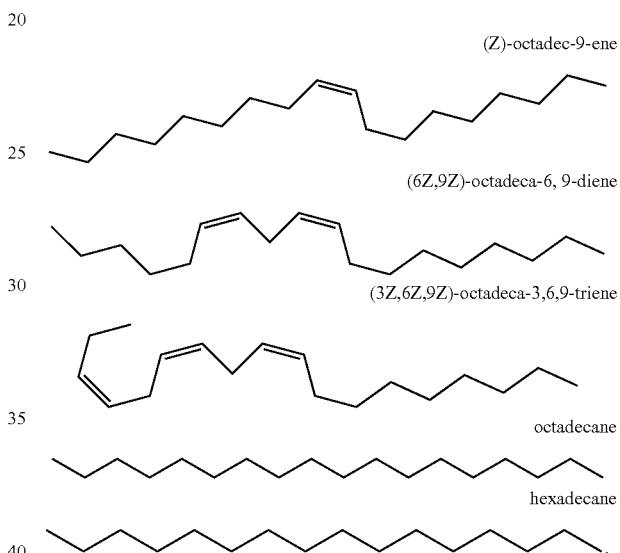

10. The polymer of claim 1, where the polymer is characterized by a number average molecular weight of from about 12.6 to 20 kDa.

11. The polymer of claim 1, where the polymer is characterized by a weight average molecular weight of from about 14.7 to about 37 kDa.

* * * * *